(12) United States Patent
Hyde et al.

(10) Patent No.: US 9,364,151 B2
(45) Date of Patent: Jun. 14, 2016

(54) QUANTIFIED-SELF MACHINES AND CIRCUITS REFLEXIVELY RELATED TO FOOD-AND-NUTRITION MACHINES AND CIRCUITS

(71) Applicant: Elwha LLC, Bellevue, WA (US)

(72) Inventors: Roderick A. Hyde, Redmond, WA (US); Muriel Y. Ishikawa, Livermore, CA (US); Jordin T. Kare, Seattle, WA (US); Eric C. Leuthardt, St. Louis, MO (US); Royce A. Levien, Lexington, MA (US); Richard T. Lord, Gig Harbor, WA (US); Robert W. Lord, Seattle, WA (US); Mark A. Malamud, Seattle, WA (US); Clarence T. Tegreene, Mercer Island, WA (US); Charles Whitmer, North Bend, WA (US); Lowell L. Wood, Jr., Bellevue, WA (US); Victoria Y. H. Wood, Livermore, CA (US); Nathan P. Myhrvold, Medina, WA (US); Elizabeth A. Sweeney, Seattle, WA (US)

(73) Assignee: Elwha LLC, Bellevue, WA (US)

(*) Notice: Subject to any disclaimer, the term of this patent is extended or adjusted under 35 U.S.C. 154(b) by 106 days.

(21) Appl. No.: 14/230,625

(22) Filed: Mar. 31, 2014

(65) Prior Publication Data

US 2015/0279185 A1   Oct. 1, 2015

(51) Int. Cl.
*G08B 1/08* (2006.01)
*A61B 5/00* (2006.01)
*A61B 5/11* (2006.01)
*G06F 19/00* (2011.01)
*A61B 5/18* (2006.01)

(52) U.S. Cl.
CPC ............. *A61B 5/0022* (2013.01); *A61B 5/1112* (2013.01); *A61B 5/1113* (2013.01); *A61B 5/6801* (2013.01); *A61B 5/6887* (2013.01); *G06F 19/3475* (2013.01); *A61B 5/18* (2013.01); *A61B 5/4806* (2013.01); *A61B 5/4833* (2013.01); *A61B 5/74* (2013.01); *A61B 2503/40* (2013.01); *A61B 2562/06* (2013.01)

(58) Field of Classification Search
CPC .................................................. G06F 19/3481
USPC ...................................................... 340/539.12
See application file for complete search history.

(56) References Cited

U.S. PATENT DOCUMENTS

| | | | | |
|---|---|---|---|---|
| 2008/0178749 A1* | 7/2008 | Stutman | ................. | G06Q 10/06 99/494 |
| 2010/0028501 A1* | 2/2010 | Baxter | ................. | G07F 17/0071 426/231 |
| 2011/0038998 A1* | 2/2011 | Kohli | ................. | A47J 31/40 426/433 |
| 2012/0322872 A1* | 12/2012 | Kraus | ................. | C07C 409/24 514/557 |
| 2014/0070957 A1* | 3/2014 | Longinotti-Buitoni | ............. | A61B 5/02055 340/870.01 |
| 2015/0087921 A1* | 3/2015 | Felix | ................. | A61B 5/04087 600/301 |
| 2015/0213232 A1* | 7/2015 | Walker, II | ............. | G06F 19/345 702/19 |

* cited by examiner

*Primary Examiner* — Naomi Small

(57) ABSTRACT

A method substantially as shown and described in the detailed description and/or drawings and/or elsewhere herein. A device substantially as shown and described in the detailed description and/or drawings and/or elsewhere herein.

18 Claims, 16 Drawing Sheets

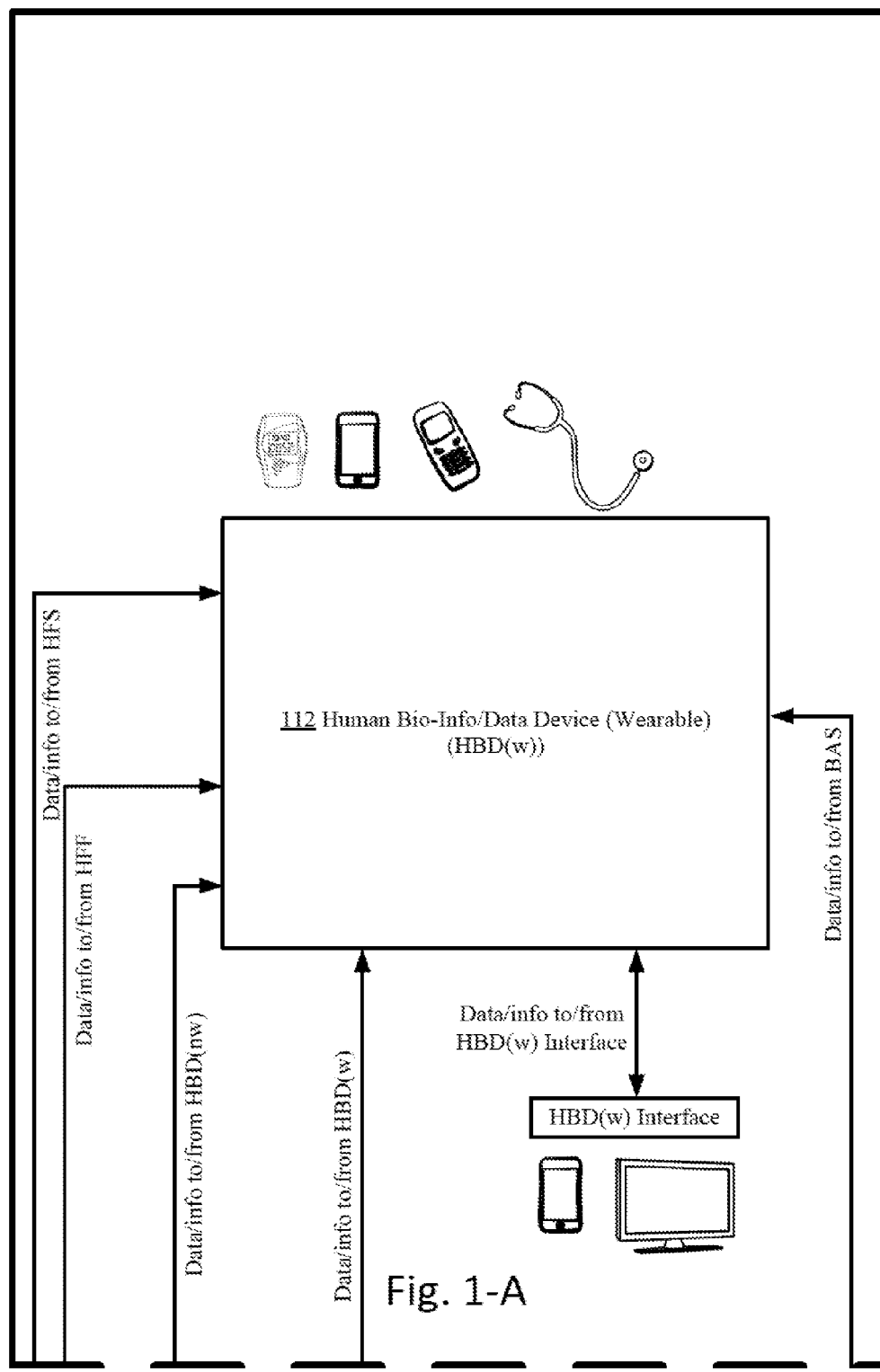
Fig. 1-A

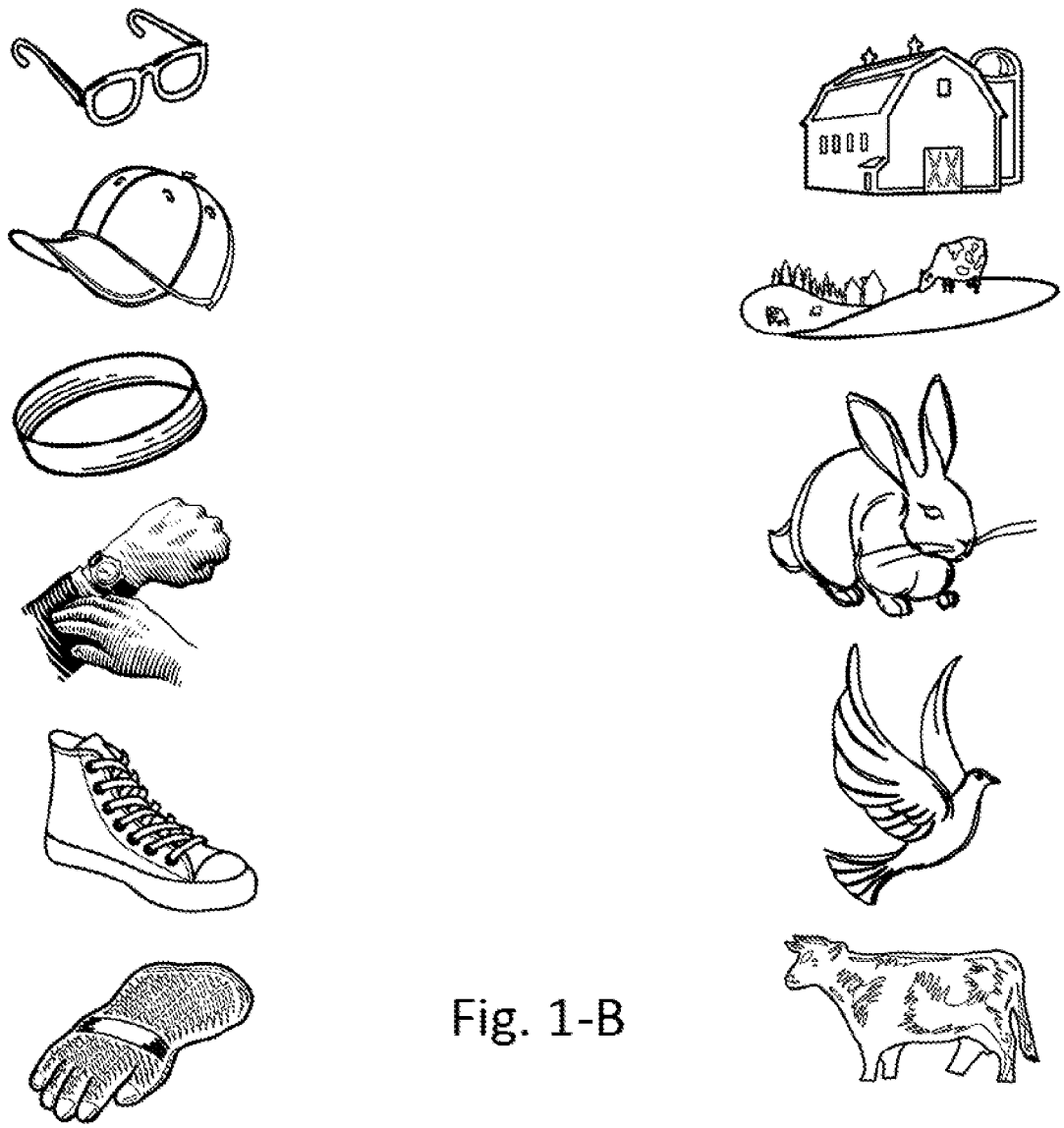
Fig. 1-B

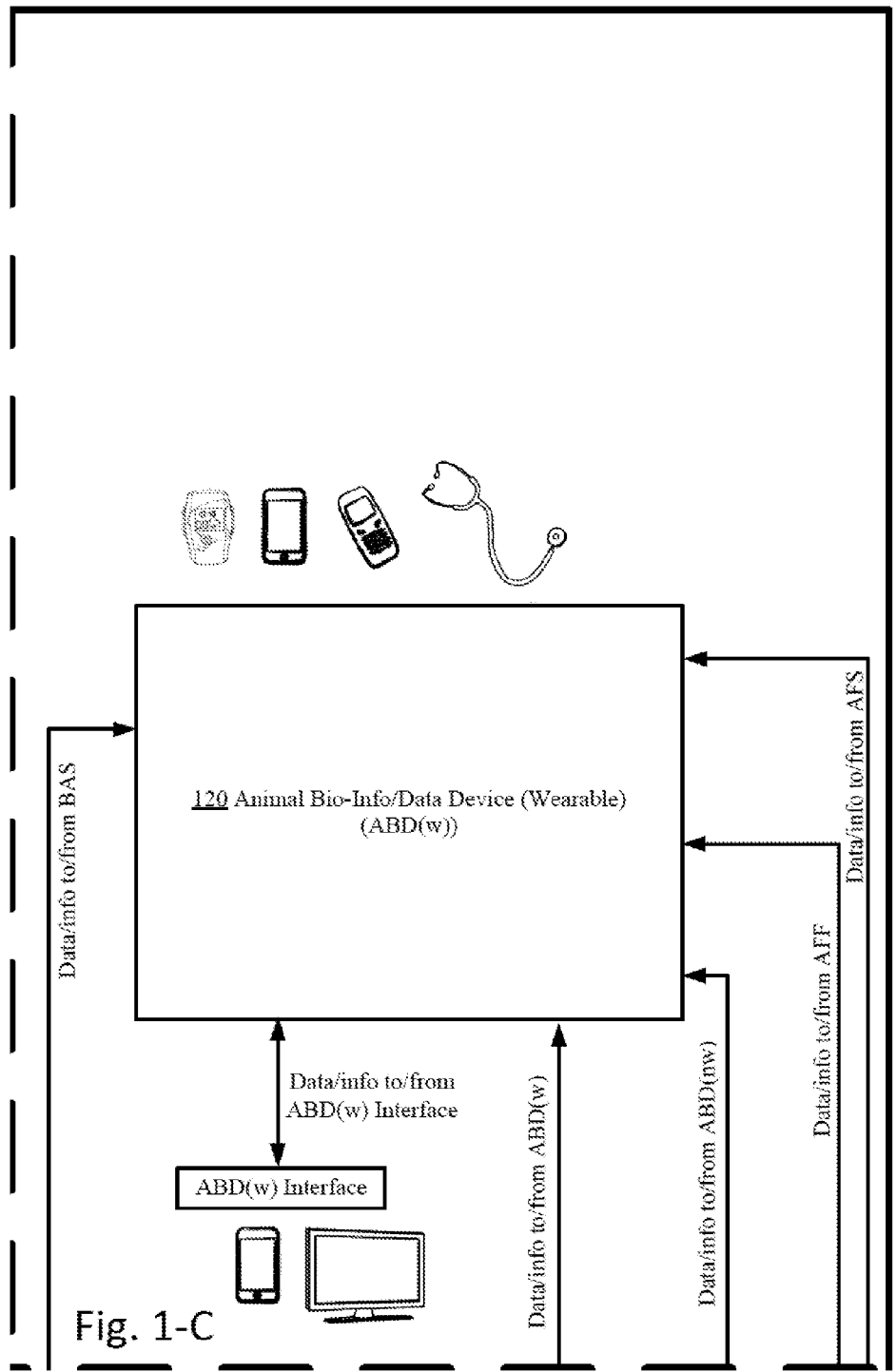
Fig. 1-C

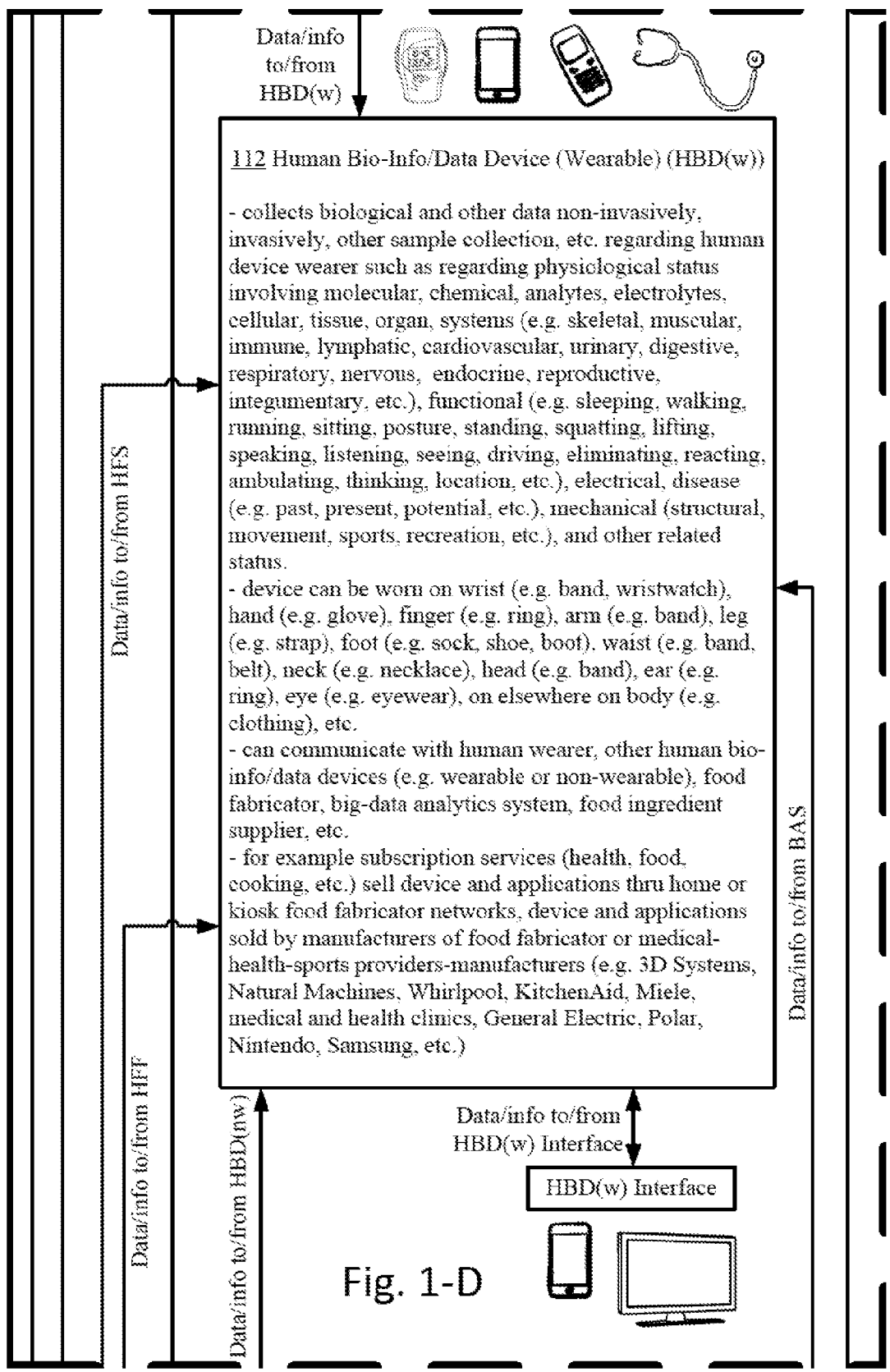
Fig. 1-D

Fig. 1-E

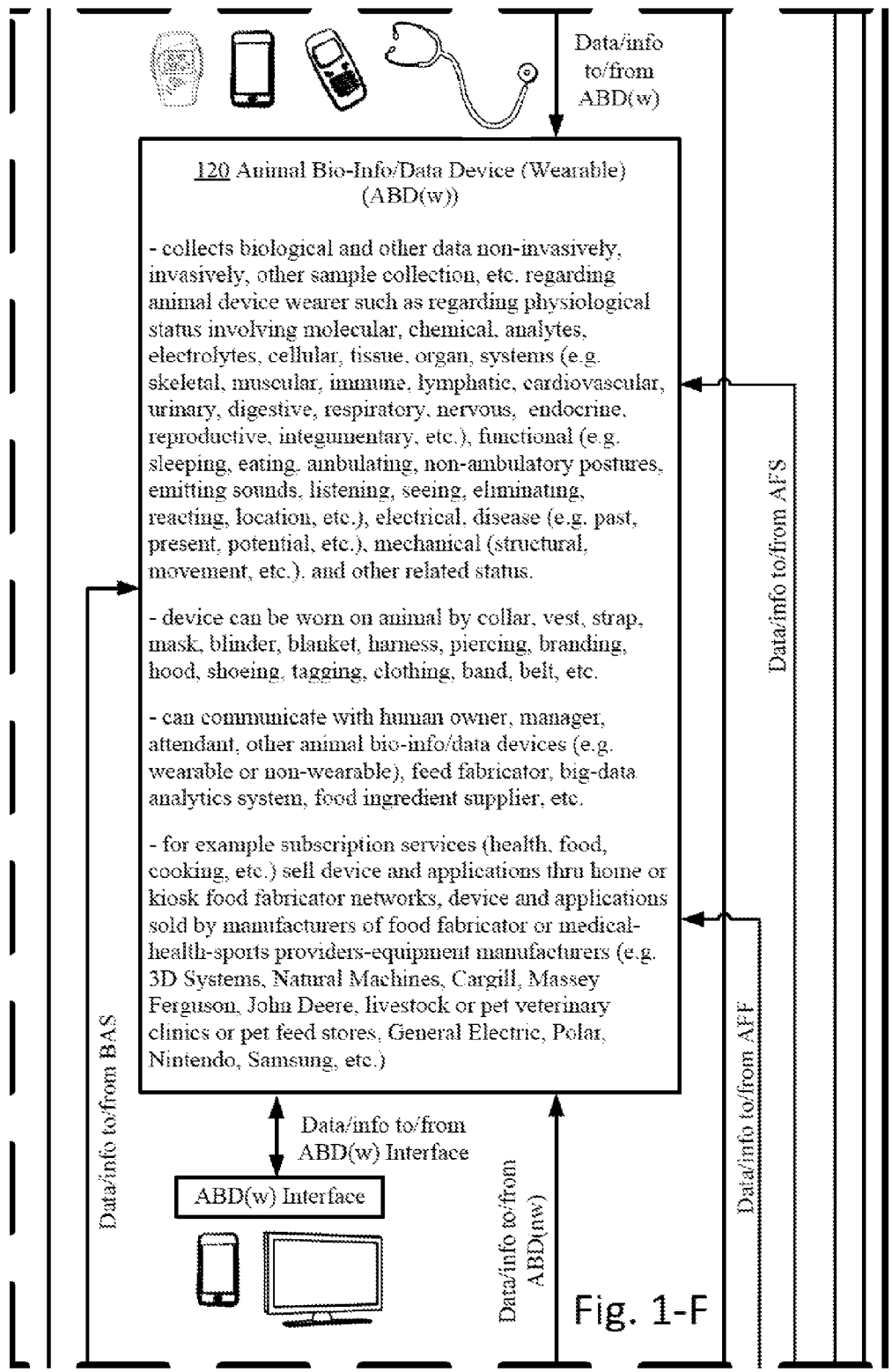
Fig. 1-F

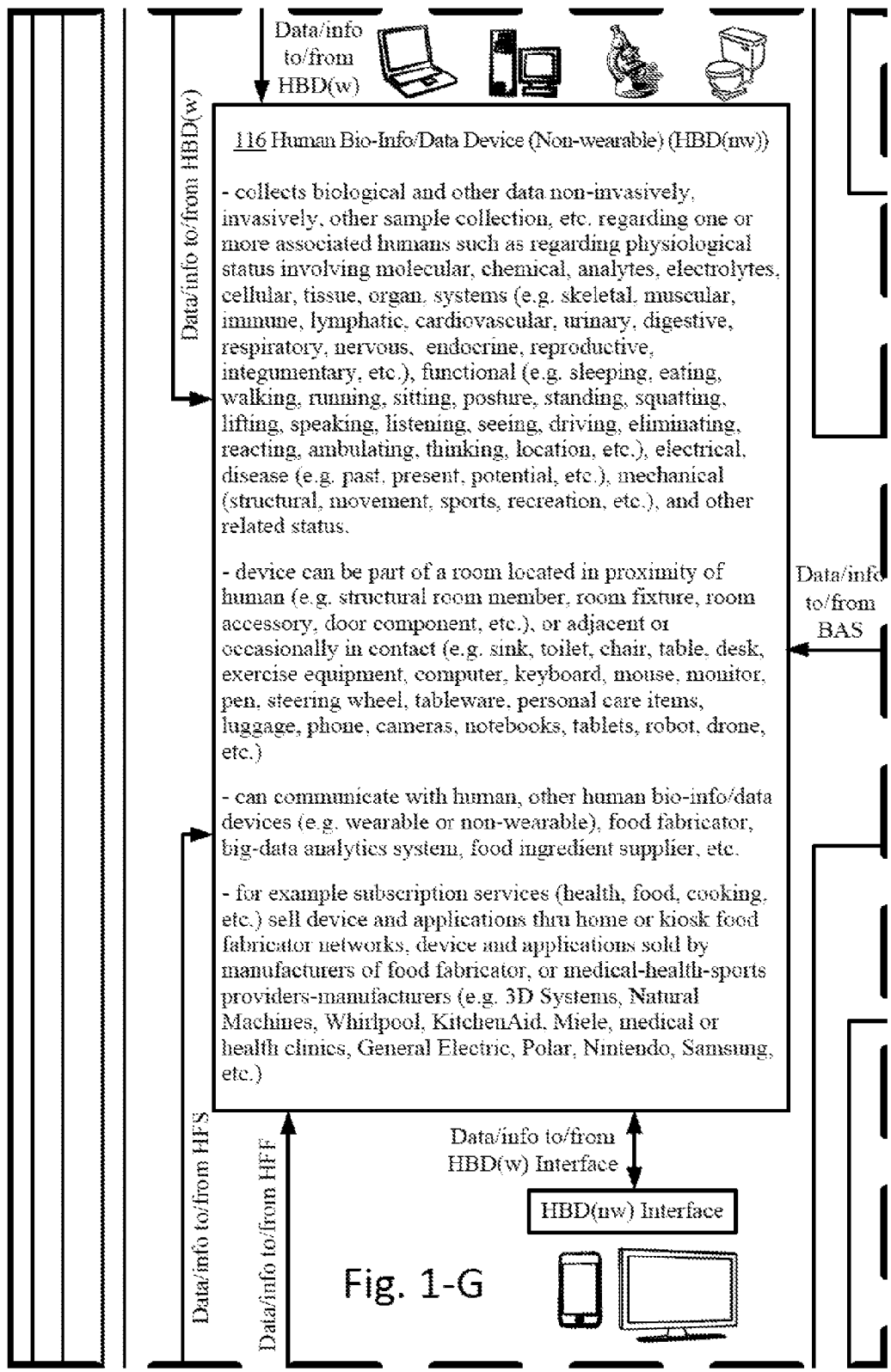
Fig. 1-G

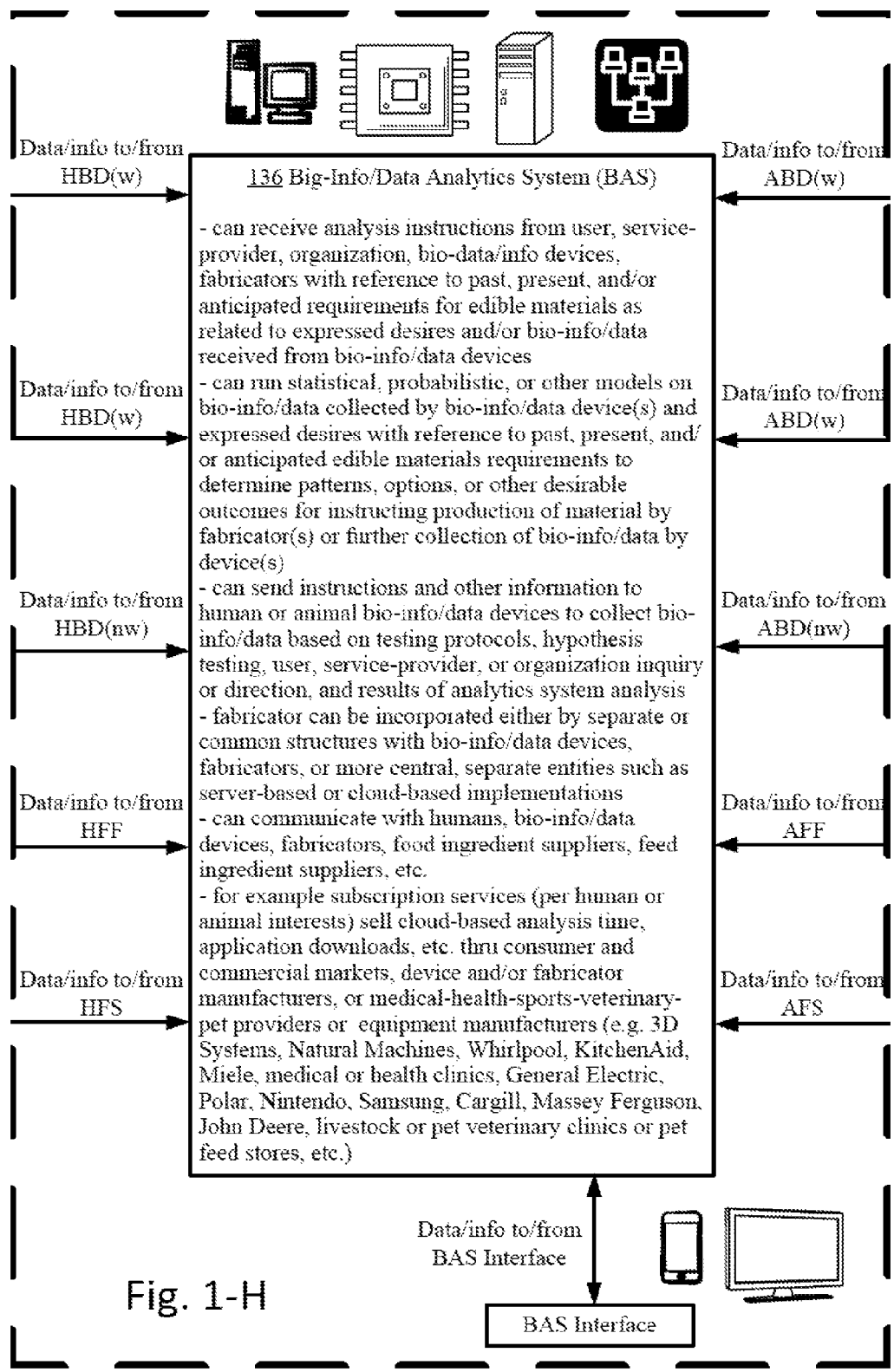
Fig. 1-H

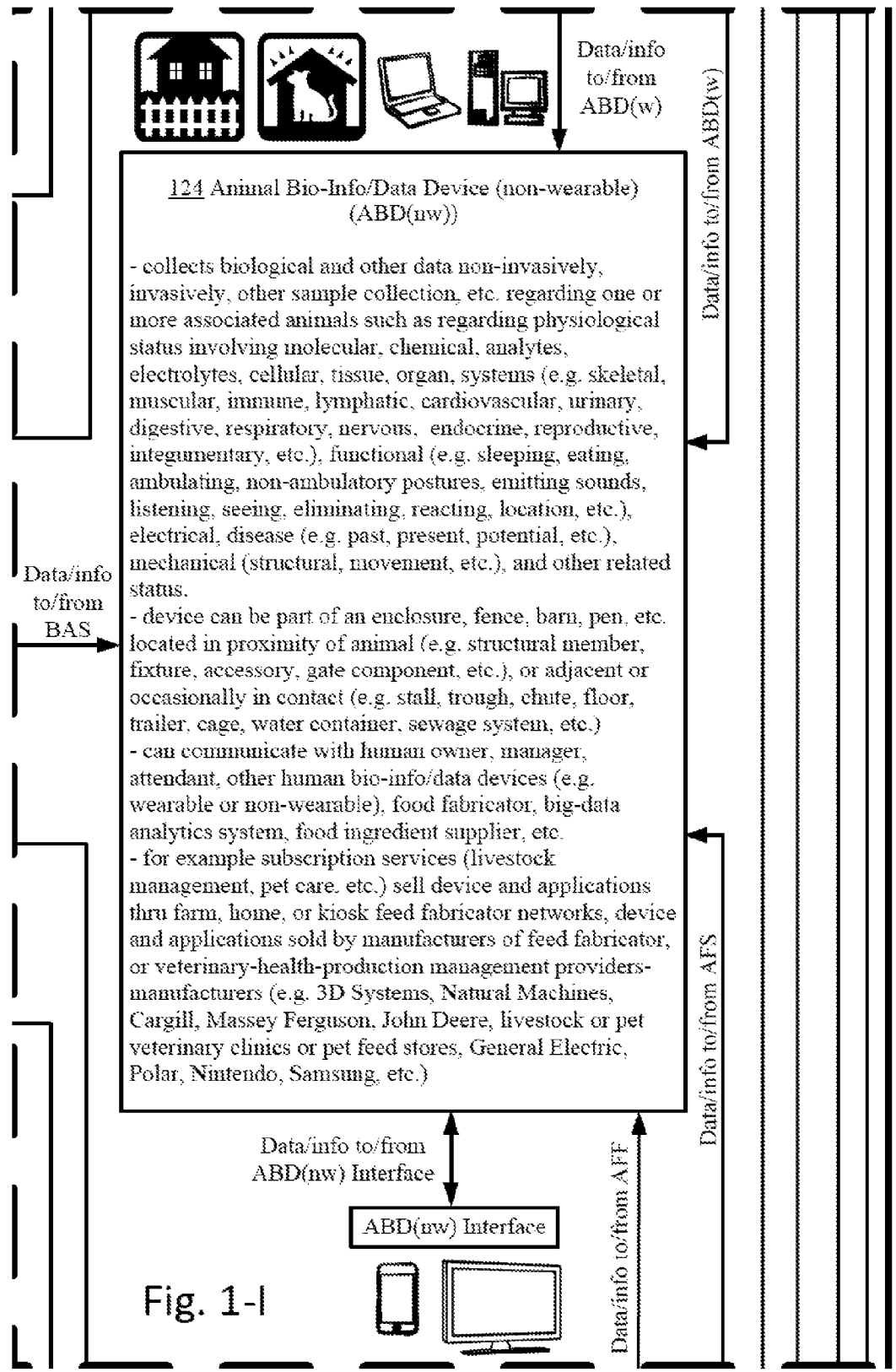
Fig. 1-I

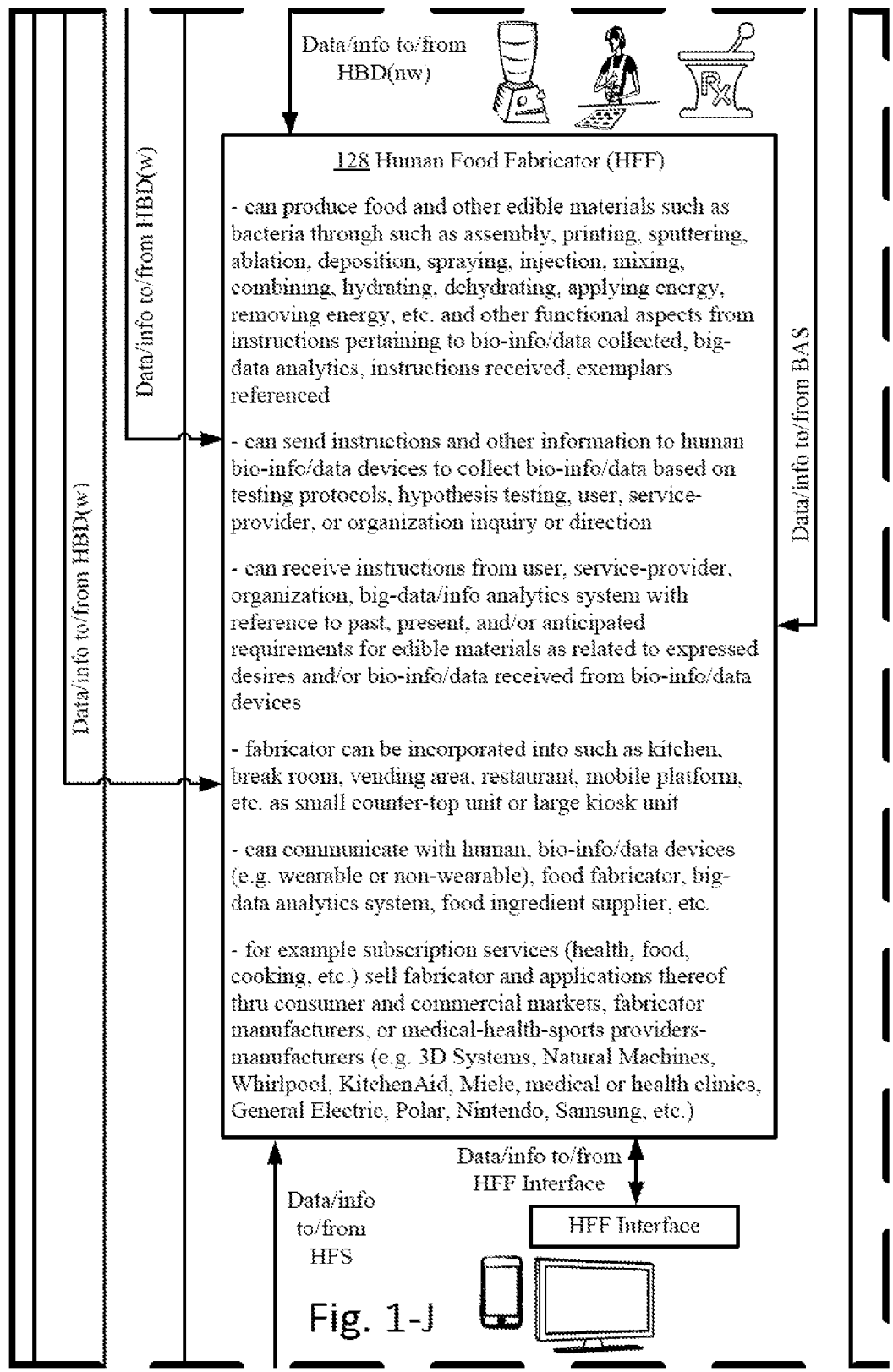
Fig. 1-J

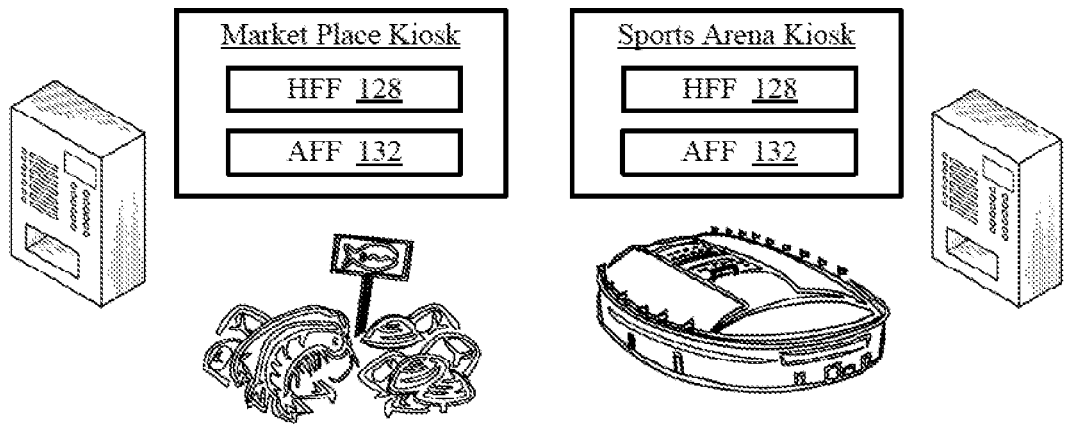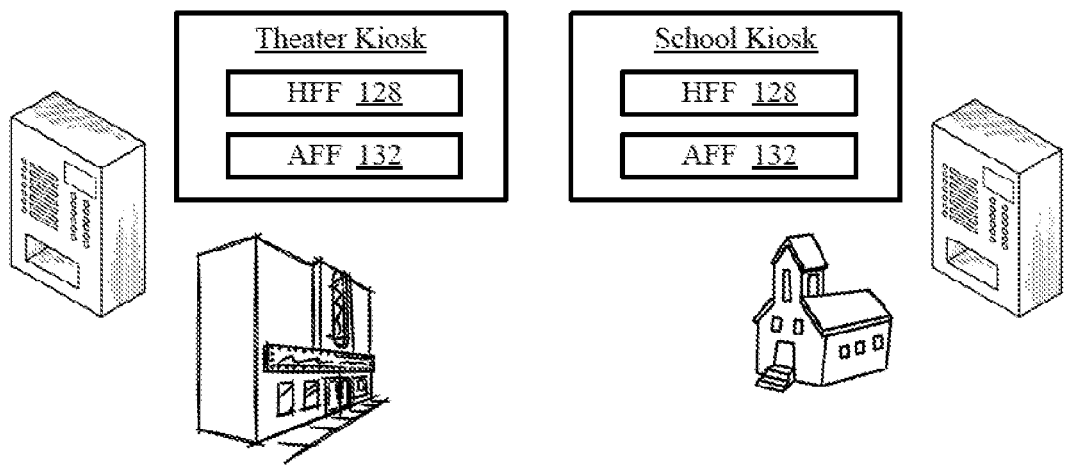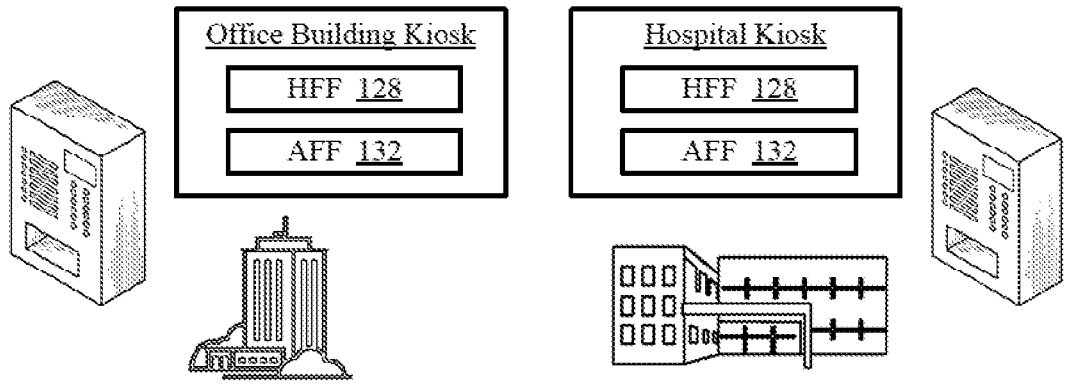
Fig. 1-K

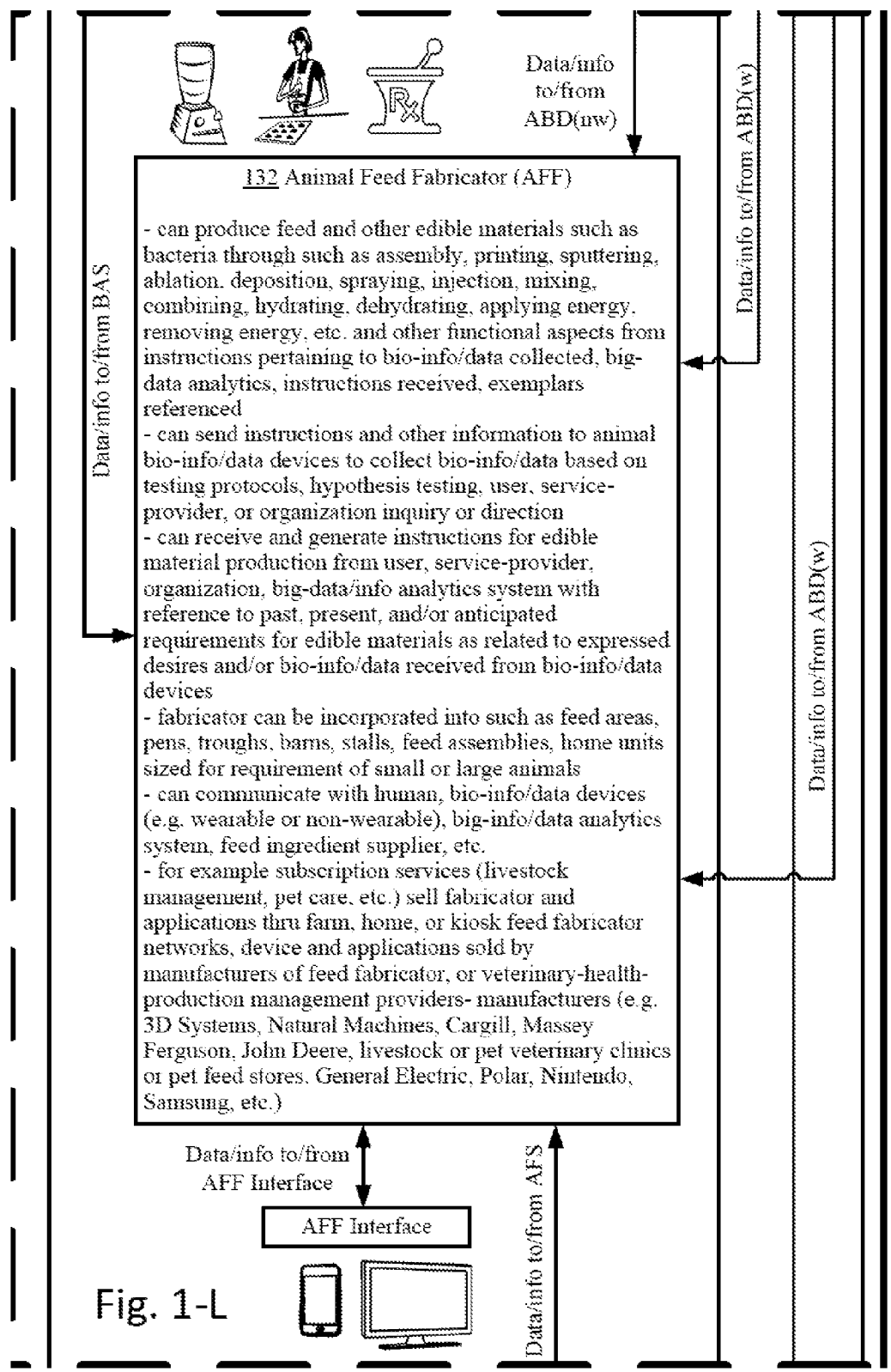
Fig. 1-L

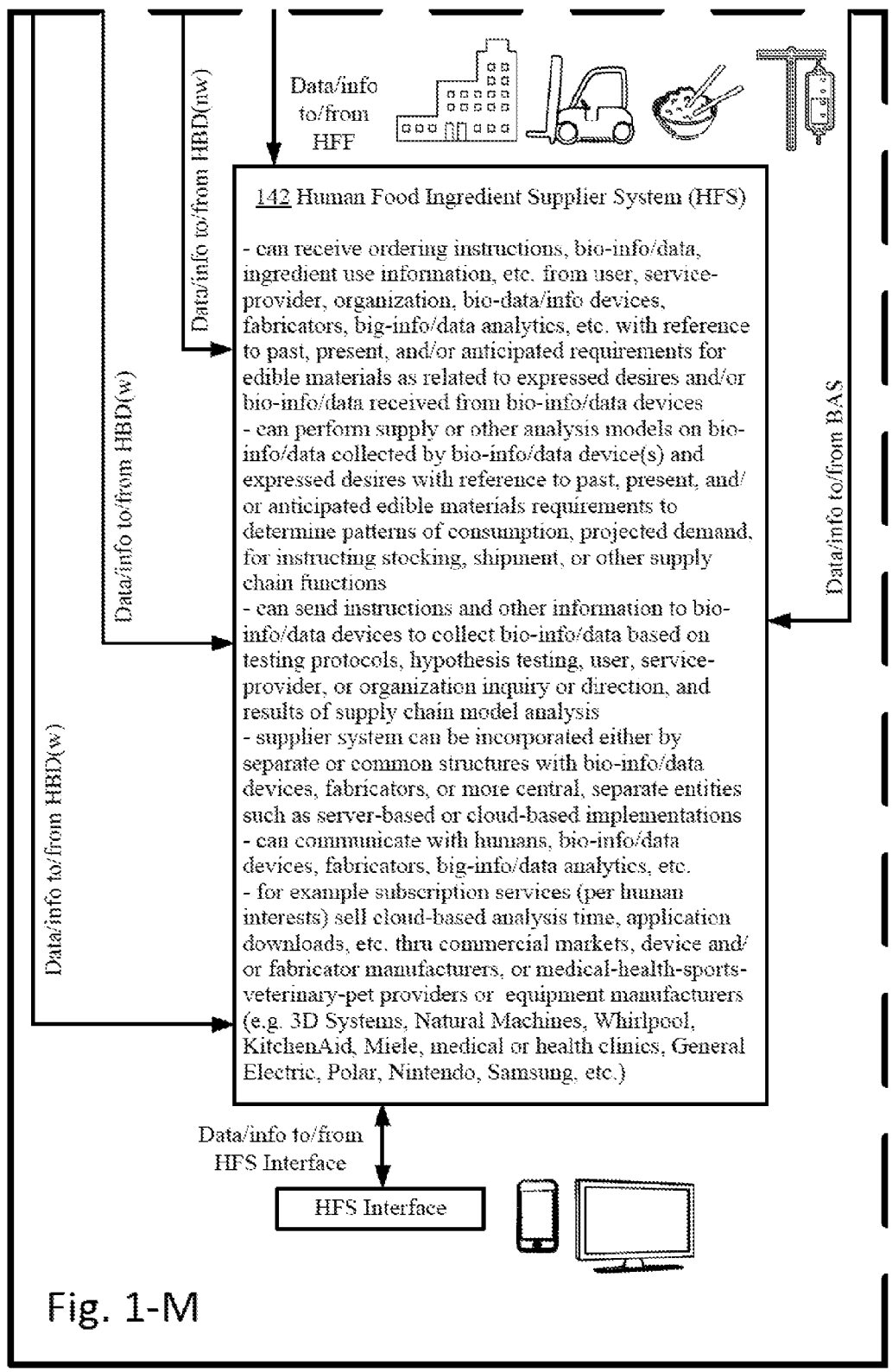
Fig. 1-M

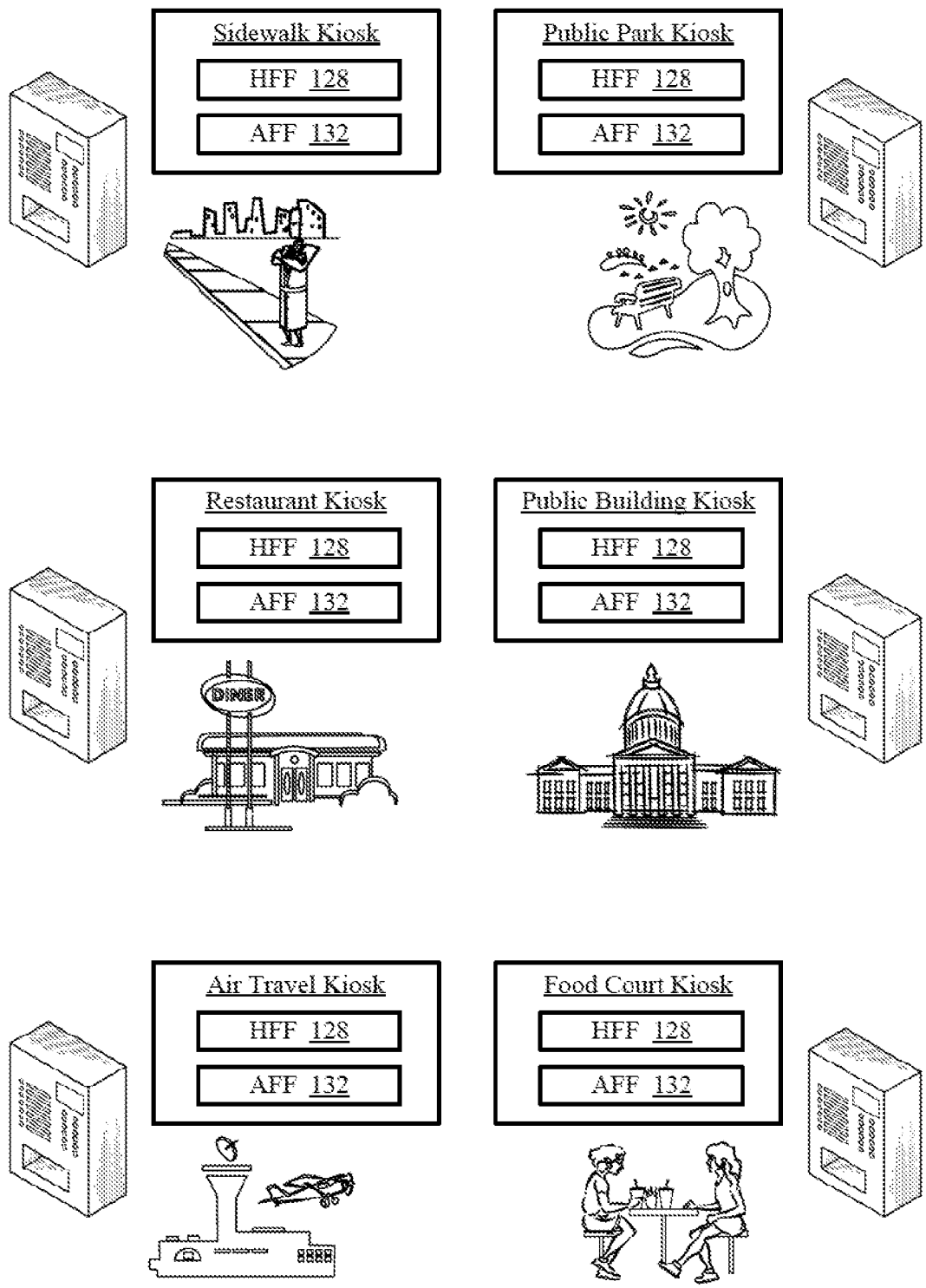
Fig. 1-N

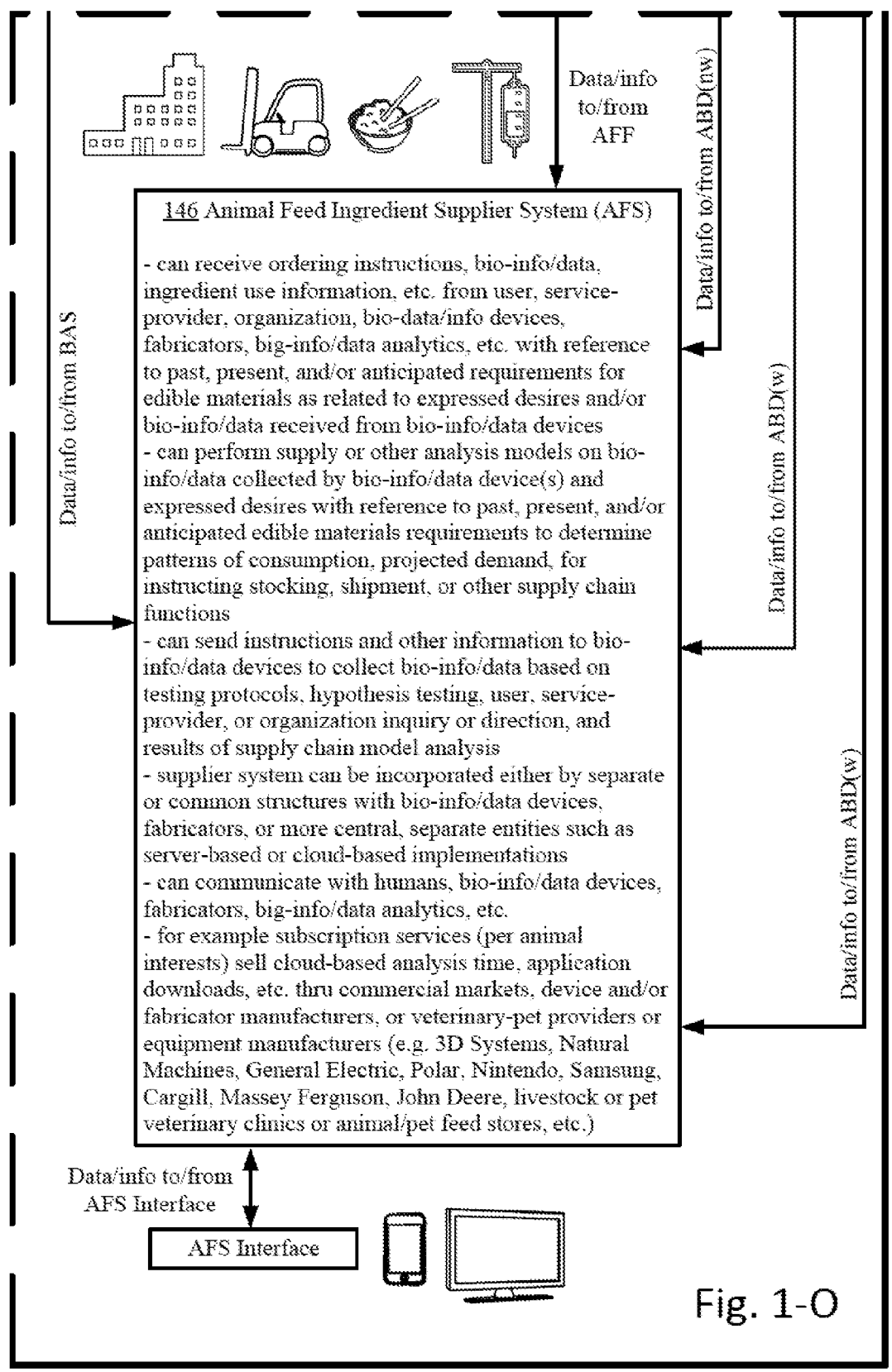
Fig. 1-O

QUANTIFIED-SELF MACHINES AND CIRCUITS REFLEXIVELY RELATED TO FOOD-AND-NUTRITION MACHINES AND CIRCUITS

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 U.S.C. §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None as of the filing date.

RELATED APPLICATIONS

None as of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

BACKGROUND

This application is related to mobile communication networks.

SUMMARY

In one or more various aspects, a method includes but is not limited to that which is illustrated in the drawings. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein-referenced method aspects. The circuitry and/or programming may be virtually any combination of hardware, software, and/or firmware configured to effect the herein-referenced method aspects depending upon the design choices of the system designer, and limited to patentable subject matter under 35 USC 101.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent by reference to the detailed description, the corresponding drawings, and/or in the teachings set forth herein.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise. The illustrative embodiments described in the detailed description, drawings, and claims are not meant to be limiting. Other embodiments may be utilized, and other changes may be made, without departing from the spirit or scope of the subject matter presented here.

In accordance with 37 C.F.R. §1.84(h)(2)

TABLE 1

Figure 1:
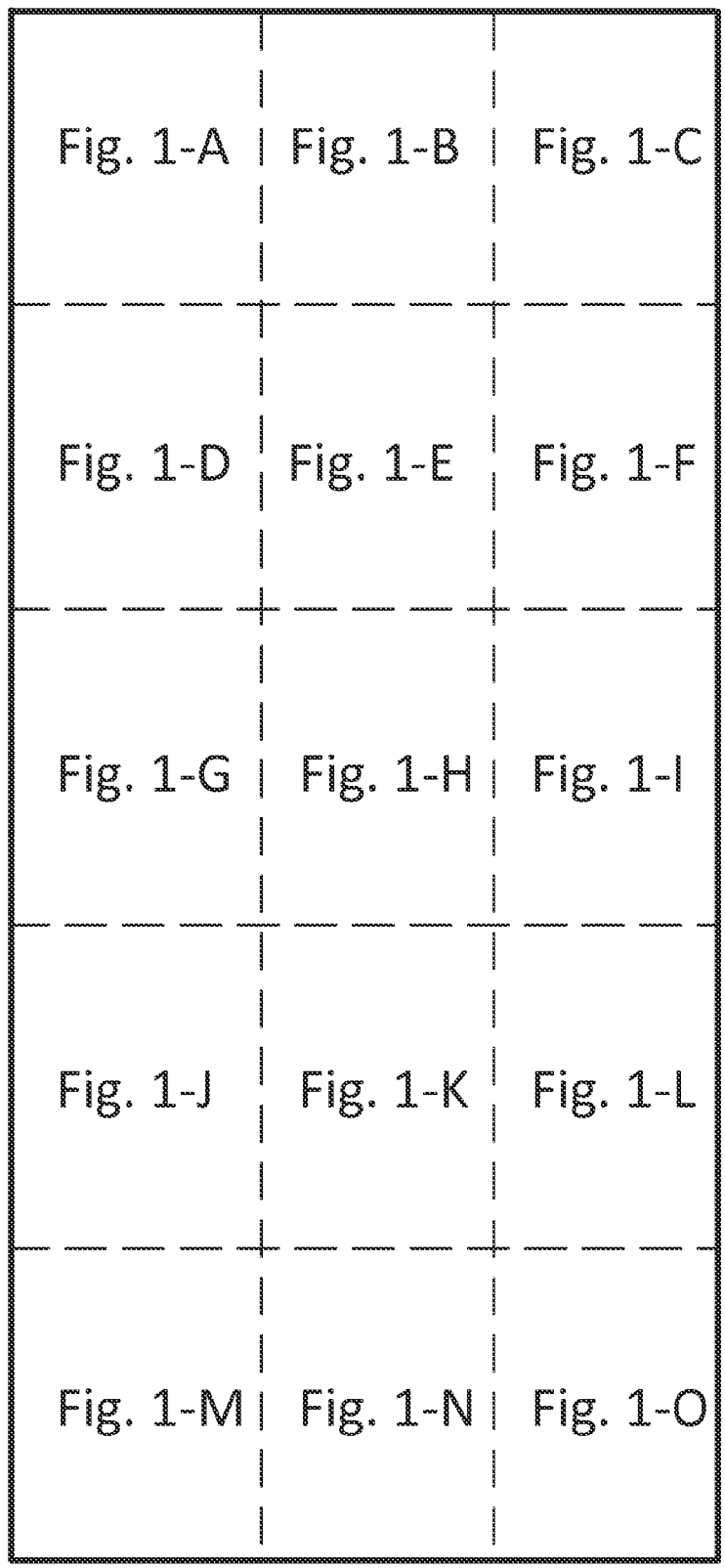
FIG. 1 shows "a view of a large machine or device in its entirety . . . broken into partial views . . . extended over several sheets" labeled FIG. 1-A through FIG. 1-O (Sheets 2-16). The "views on two or more sheets form, in effect, a single complete view, [and] the views on the several sheets . . . [are] so arranged that the complete figure can be assembled" from "partial views drawn on separate sheets . . . linked edge to edge. Thus, in FIG. 1, (i) a "smaller scale view" is "included, showing the whole formed by the partial views and indicating the positions of the parts shown," and shown in FIG. 1, e.g., as described in 37 C.F.R. §1.84(h)(2), and (ii) the partial view FIGS. 1-A through 1-O are ordered alphabetically, by increasing in columns from left to right, and increasing in rows top to bottom, as shown in the following table.

Table showing alignment of enclosed partial view drawings to form a single complete view of one or more environments.

| (1, 1)—FIG. 1-A | (1, 2)—FIG. 1-B | (1, 3)—FIG. 1-C |
| --- | --- | --- |
| (2, 1)—FIG. 1-D | (2, 2)—FIG. 1-E | (2, 3)—FIG. 1-F |
| (3, 1)—FIG. 1-G | (3, 2)—FIG. 1-H | (3, 3)—FIG. 1-I |
| (4, 1)—FIG. 1-J | (4, 2)—FIG. 1-K | (4, 3)—FIG. 1-L |
| (5, 1)—FIG. 1-M | (5, 2)—FIG. 1-N | (5, 3)—FIG. 1-O |

In accordance with 37 C.F.R. §1.84(h)(2), FIG. 1 is " . . . a view of a large machine or device in its entirety . . . broken into partial views . . . extended over several sheets . . . [with] no loss in facility of understanding the view." The partial views drawn on the several sheets indicated in the above table are capable of being linked edge to edge, so that no partial view contains parts of another partial view. As here, "where views on two or more sheets form, in effect, a single complete view, the views on the several sheets are so arranged that the complete figure can be assembled without concealing any part of any of the views appearing on the various sheets." 37 C.F.R. §1.84(h)(2).

It is noted that one or more of the partial views of the drawings may be blank, or may not contain substantive elements (e.g., may show only lines, connectors, and the like). These drawings are included in order to assist readers of the application in assembling the single complete view from the partial sheet format required for submission by the USPTO, and, while their inclusion is not required and may be omitted in this or other applications, their inclusion is proper, and should be considered intentional.

FIG. 1-A, when placed at position (1,1), forms at least a portion of a partially schematic diagram of an environment(s) and/or an implementation(s) of technologies described herein.

FIG. 1-B, when placed at position (1,2), forms at least a portion of a partially schematic diagram of an environment(s) and/or an implementation(s) of technologies described herein.

FIG. 1-C, when placed at position (1,3), forms at least a portion of a partially schematic diagram of an environment(s) and/or an implementation(s) of technologies described herein.

FIG. 1-D, when placed at position (2,1), forms at least a portion of a partially schematic diagram of an environment(s) and/or an implementation(s) of technologies described herein.

FIG. 1-E, when placed at position (2,2), forms at least a portion of a partially schematic diagram of an environment(s) and/or an implementation(s) of technologies described herein.

FIG. 1-F, when placed at position (2,3), forms at least a portion of a partially schematic diagram of an environment(s) and/or an implementation(s) of technologies described herein.

FIG. 1-G, when placed at position (3,1), forms at least a portion of a partially schematic diagram of an environment(s) and/or an implementation(s) of technologies described herein.

FIG. 1-H, when placed at position (3,2), forms at least a portion of a partially schematic diagram of an environment(s) and/or an implementation(s) of technologies described herein.

FIG. 1-I, when placed at position (3,3), forms at least a portion of a partially schematic diagram of an environment(s) and/or an implementation(s) of technologies described herein.

FIG. 1-J, when placed at position (4,1), forms at least a portion of a partially schematic diagram of an environment(s) and/or an implementation(s) of technologies described herein.

FIG. 1-K, when placed at position (4,2), forms at least a portion of a partially schematic diagram of an environment(s) and/or an implementation(s) of technologies described herein.

FIG. 1-L, when placed at position (4,3), forms at least a portion of a partially schematic diagram of an environment(s) and/or an implementation(s) of technologies described herein.

FIG. 1-M, when placed at position (5,1), forms at least a portion of a partially schematic diagram of an environment(s) and/or an implementation(s) of technologies described herein.

FIG. 1-N, when placed at position (5,2), forms at least a portion of a partially schematic diagram of an environment(s) and/or an implementation(s) of technologies described herein.

FIG. 1-O, when placed at position (5,3), forms at least a portion of a partially schematic diagram of an environment(s) and/or an implementation(s) of technologies described herein.

DETAILED DESCRIPTION

The present application uses formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

In the following detailed description, reference is made to the accompanying drawings, which form a part hereof. In the drawings, similar symbols typically identify similar or identical components or items, unless context dictates otherwise. The illustrative embodiments described in the detailed description, drawings, and claims are not meant to be limiting. Other embodiments may be utilized, and other changes may be made, without departing from the spirit or scope of the subject matter presented here.

Thus, in accordance with various embodiments, computationally implemented methods, systems, circuitry, articles of manufacture, ordered chains of matter, and computer program products are designed to, among other things, provide an interface for the environment illustrated in FIG. 1.

The claims, description, and drawings of this application may describe one or more of the instant technologies in operational/functional language, for example as a set of operations to be performed by a computer. Such operational/functional description in most instances would be understood by one skilled the art as specifically-configured hardware (e.g., because a general purpose computer in effect becomes a special purpose computer once it is programmed to perform particular functions pursuant to instructions from program software (e.g., a high-level computer program serving as a hardware specification)).

Importantly, although the operational/functional descriptions described herein are understandable by the human mind, they are not abstract ideas of the operations/functions divorced from computational implementation of those operations/functions. Rather, the operations/functions represent a specification for massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to a human reader. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail herein, these logical operations/functions are not representations of abstract ideas, but rather are representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct" (e.g., that "software"—a computer program or computer programming—is somehow an ineffable mental construct, because at a high level of abstraction, it can be conceived and understood by a human reader). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of logic, such as Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configurations, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, http://en.wikipedia.org/wiki/Instructions_per_second (as of Jun. 5, 2012, 21:04 GMT). Thus, programs written in machine language—which may be tens of millions of machine language instructions long—are incomprehensible to most humans. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that useful, tangible, and concrete work is done. For example, as indicated above, such machine language—the compiled version of the higher-level language—functions as a technical specification which selects out hardware logic gates, specifies voltage levels, voltage transition timings, etc., such that the useful work is accomplished by the hardware.

Thus, a functional/operational technical description, when viewed by one of skill in the art, is far from an abstract idea.

Rather, such a functional/operational technical description, when understood through the tools available in the art such as those just described, is instead understood to be a humanly understandable representation of a hardware specification, the complexity and specificity of which far exceeds the comprehension of most any one human. With this in mind, those skilled in the art will understand that any such operational/functional technical descriptions—in view of the disclosures herein and the knowledge of those skilled in the art—may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality of logic(s), or (d) virtually any combination of the foregoing. Indeed, any physical object which has a stable, measurable, and changeable state may be used to construct a machine based on the above technical description. Charles Babbage, for example, constructed the first mechanized computational apparatus out of wood, with the apparatus powered by cranking a handle.

Thus, far from being understood as an abstract idea, those skilled in the art will recognize a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language should not be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/ functions disclosed herein should be treated as such, and should not be disparagingly characterized as abstract ideas merely because the specifications they represent are presented in a manner that one of skill in the art can readily understand and apply in a manner independent of a specific vendor's hardware implementation.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Those having skill in the art will recognize that the state of the art has progressed to the point where there is little distinction left between hardware, software (e.g., a high-level computer program serving as a hardware specification), and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software (e.g., a high-level computer program serving as a hardware specification), and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software (e.g., a high-level computer program serving as a hardware specification) implementation; or, yet again alternatively, the implementer may opt for some combination of hardware, software (e.g., a high-level computer program serving as a hardware specification), and/or firmware in one or more machines, compositions of matter, and articles of manufacture, limited to patentable subject matter under 35 U.S.C. §101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software (e.g., a high-level computer program serving as a hardware specification), and or firmware.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software (e.g., a high-level computer program serving as a hardware specification) or firmware, or of gate arrays or programmable hardware, such as by performing a reception of or a transmission of one or more instructions in relation to one or more operations described herein. Alternatively or additionally, in some variants, an implementation may include special-purpose hardware, software (e.g., a high-level computer program serving as a hardware specification), firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/ converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software (e.g., a high-level computer program serving as a hardware specification), firmware, or virtually any combination thereof, limited to patentable subject matter under 35 U.S.C. 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. 101, and that designing the circuitry and/or writing the code for the software (e.g., a high-level computer program serving as a hardware specification) and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The term module, as used in the foregoing/following disclosure, may refer to a collection of one or more components that are arranged in a particular manner, or a collection of one or more general-purpose components that may be configured to operate in a particular manner at one or more particular points in time, and/or also configured to operate in one or more further manners at one or more further times. For example, the same hardware, or same portions of hardware, may be configured/reconfigured in sequential/parallel time(s) as a first type of module (e.g., at a first time), as a second type of module (e.g., at a second time, which may in some instances coincide with, overlap, or follow a first time), and/or as a third type of module (e.g., at a third time which may, in some instances, coincide with, overlap, or follow a first time and/or a second time), etc. Reconfigurable and/or controllable components (e.g., general purpose processors, digital signal processors, field programmable gate arrays, etc.) are capable of being configured as a first module that has a first purpose, then a second module that has a second purpose and then, a third module that has a third purpose, and so on. The transition of a reconfigurable and/or controllable component may occur in as little as a few nanoseconds, or may occur over a period of minutes, hours, or days.

In some such examples, at the time the component is configured to carry out the second purpose, the component may no longer be capable of carrying out that first purpose until it is reconfigured. A component may switch between configurations as different modules in as little as a few nanoseconds. A component may reconfigure on-the-fly, e.g., the reconfiguration of a component from a first module into a second module may occur just as the second module is needed. A component may reconfigure in stages, e.g., portions of a first module that are no longer needed may reconfigure into the second module even before the first module has finished its operation. Such reconfigurations may occur automatically, or may occur through prompting by an external source, whether that source is another component, an instruction, a signal, a condition, an external stimulus, or similar.

For example, a central processing unit of a personal computer may, at various times, operate as a module for displaying graphics on a screen, a module for writing data to a storage medium, a module for receiving user input, and a module for multiplying two large prime numbers, by configuring its logical gates in accordance with its instructions. Such reconfiguration may be invisible to the naked eye, and in some embodiments may include activation, deactivation, and/or re-routing of various portions of the component, e.g., switches, logic gates, inputs, and/or outputs. Thus, in the examples found in the foregoing/following disclosure, if an example includes or recites multiple modules, the example includes the possibility that the same hardware may implement more than one of the recited modules, either contemporaneously or at discrete times or timings. The implementation of multiple modules, whether using more components, fewer components, or the same number of components as the number of modules, is merely an implementation choice and does not generally affect the operation of the modules themselves. Accordingly, it should be understood that any recitation of multiple discrete modules in this disclosure includes implementations of those modules as any number of underlying components, including, but not limited to, a single component that reconfigures itself over time to carry out the functions of multiple modules, and/or multiple components that similarly reconfigure, and/or special purpose reconfigurable components.

In a general sense, those skilled in the art will recognize that the various embodiments described herein can be implemented, individually and/or collectively, by various types of electro-mechanical systems having a wide range of electrical components such as hardware, software (e.g., a high-level computer program serving as a hardware specification), firmware, and/or virtually any combination thereof, limited to patentable subject matter under 35 U.S.C. 101; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software (e.g., a high-level computer program serving as a hardware specification), firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software (e.g., a high-level computer program serving as a hardware specification), and/or firmware.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, Verizon, AT&T, etc.), or (g) a wired/wireless services entity (e.g., Sprint, AT&T, Verizon, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user XXX is shown/described herein as a single illustrated figure, those skilled in the art will appreciate that user XXX may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g., "configured to") generally encompass active-state components and/or inactive-state components and/or standby-state components, unless context requires otherwise.

For the purposes of this application, "cloud" computing may be understood as described in the cloud computing literature. For example, cloud computing may be methods and/or systems for the delivery of computational capacity and/or storage capacity as a service. The "cloud" may refer to one or more hardware and/or software (e.g., a high-level computer program serving as a hardware specification) components that deliver or assist in the delivery of computational and/or storage capacity, including, but not limited to, one or more of a client, an application, a platform, an infrastructure, and/or a server. The cloud may refer to any of the hardware and/or software (e.g., a high-level computer program serving as a hardware specification) associated with a client, an application, a platform, an infrastructure, and/or a server. For example, cloud and cloud computing may refer to one or more of a computer, a processor, a storage medium, a router, a switch, a modem, a virtual machine (e.g., a virtual server), a data center, an operating system, a middleware, a firmware, a hardware back-end, an application back-end, and/or a programmed application. A cloud may refer to a private cloud, a public cloud, a hybrid cloud, and/or a community cloud. A cloud may be a shared pool of configurable computing resources, which may be public, private, semi-private, distributable, scaleable, flexible, temporary, virtual, and/or physical. A cloud or cloud service may be delivered over one or more types of network, e.g., a mobile communication network, and the Internet.

As used in this application, a cloud or a cloud service may include one or more of infrastructure-as-a-service ("IaaS"), platform-as-a-service ("PaaS"), software-as-a-service ("SaaS"), and/or desktop-as-a-service ("DaaS"). As a non-exclusive example, IaaS may include, e.g., one or more virtual server instantiations that may start, stop, access, and/or configure virtual servers and/or storage centers (e.g., providing one or more processors, storage space, and/or network resources on-demand, e.g., EMC and Rackspace). PaaS may include, e.g., one or more program, module, and/or development tools hosted on an infrastructure (e.g., a computing platform and/or a solution stack from which the client can create software-based interfaces and applications, e.g., Microsoft Azure). SaaS may include, e.g., software hosted by a service provider and accessible over a network (e.g., the software for the application and/or the data associated with that software application may be kept on the network, e.g., Google Apps, SalesForce). DaaS may include, e.g., providing desktop, applications, data, and/or services for the user over a network (e.g., providing a multi-application framework, the applications in the framework, the data associated with the applications, and/or services related to the applications and/or the data over the network, e.g., Citrix). The foregoing is intended to be exemplary of the types of systems and/or methods referred to in this application as "cloud" or "cloud computing" and should not be considered complete or exhaustive.

As depicted in FIG. 1, a quantified-self information system regarding quantified-self information and data such as human bio-info/data and animal bio-info/data includes human bio-info/data devices (wearable) 112, human bio-info/data devices (non-wearable) 116, animal bio-info/data devices (wearable) 120, animal bio-info/data devices (non-wearable) 124, human food fabricators 128, animal feed fabricators 132, big-info/data analytics system 136, human food ingredient supplier systems 142, and animal feed ingredient supplier systems 146 electronically communicatively linked together for information and data collection, analysis and operational guidance thereby, and other interrelated functionality therebetween.

The human bio-info/data device (wearable) 112 can include the following. The human bio-info/data device (wearable) 112 can collect biological and other data non-invasively, invasively, other sample collection, etc. regarding human device wearer such as regarding physiological status involving molecular, chemical, analytes, electrolytes, cellular, tissue, organ, systems (e.g., skeletal, muscular, immune, lymphatic, cardiovascular, urinary, digestive, respiratory, nervous, endocrine, reproductive, integumentary, etc.), functional (e.g., sleeping, walking, running, sitting, posture, standing, squatting, lifting, speaking, listening, seeing, driving, eliminating, reacting, ambulating, thinking, location, etc.), electrical, disease (e.g., past, present, potential, etc.), mechanical (structural, movement, sports, recreation, etc.), and other related status.

The human bio-info/data device (wearable) 112 can be worn on wrist (e.g., band, wristwatch), hand (e.g., glove), finger (e.g., ring), arm (e.g., band), leg (e.g., strap), foot (e.g., sock, shoe, boot), waist (e.g., band, belt), neck (e.g., necklace), head (e.g., band), ear (e.g., ring), eye (e.g., eyewear), on elsewhere on body (e.g., clothing), etc.

The human bio-info/data device (wearable) 112 can communicate with human wearer, other human bio-info/data devices (e.g., wearable or non-wearable), food fabricator, big-data analytics system, food ingredient supplier, etc.

The human bio-info/data device (wearable) 112 can include for example subscription services (health, food, cooking, etc.) sell device and applications thru home or kiosk food fabricator networks, device and applications sold by manufacturers of food fabricator or medical-health-sports providers-manufacturers (e.g., 3D Systems, Natural Machines, Whirlpool, KitchenAid, Miele, medical and health clinics, General Electric, Polar, Nintendo, Samsung, etc.).

The human bio-info/data device (non-wearable) 116 can include the following. The human bio-info/data device (non-wearable) 116 can collect biological and other data non-invasively, invasively, other sample collection, etc. regarding one or more associated humans such as regarding physiological status involving molecular, chemical, analytes, electrolytes, cellular, tissue, organ, systems (e.g., skeletal, muscular, immune, lymphatic, cardiovascular, urinary, digestive, respiratory, nervous, endocrine, reproductive, integumentary, etc.), functional (e.g., sleeping, eating, walking, running, sitting, posture, standing, squatting, lifting, speaking, listening, seeing, driving, eliminating, reacting, ambulating, thinking, location, etc.), electrical, disease (e.g., past, present, potential, etc.), mechanical (structural, movement, sports, recreation, etc.), and other related status.

The human bio-info/data device (non-wearable) 116 can be part of a room located in proximity of human (e.g., structural room member, room fixture, room accessory, door component, etc.), or adjacent or occasionally in contact (e.g., sink, toilet, chair, table, desk, exercise equipment, computer, keyboard, mouse, monitor, pen, steering wheel, tableware, personal care items, luggage, phone, cameras, notebooks, tablets, robot, drone, etc.).

The human bio-info/data device (non-wearable) 116 can communicate with human, other human bio-info/data devices (e.g., wearable or non-wearable), food fabricator, big-data analytics system, food ingredient supplier, etc.

The human bio-info/data device (non-wearable) 116 for example subscription services (health, food, cooking, etc.) sell device and applications thru home or kiosk food fabricator networks, device and applications sold by manufacturers of food fabricator, or medical-health-sports providers-manufacturers (e.g., 3D Systems, Natural Machines, Whirlpool, KitchenAid, Miele, medical or health clinics, General Electric, Polar, Nintendo, Samsung, etc.).

Further aspects regarding the wearable and non-wearable human bio-info/data devices can include collecting information or data related to food preferences such as texture, color, or taste such as sweet, sour, salty, or other taste sensations. Such collected information or data can in a sense profile a particular individual as far as how the individual reacts to various foods and other indigestible materials from a psychological, physiological, sensory, or other aspects. This type of profiling can then be used in order to tailor the various food and other indigestible materials for the individual. For instance, the profiling information can be used to tune macronutrient, micronutrient, bacterial or other content of food in real time regarding various activity levels of the individual. These activity levels can be related to environmental conditions such as weather conditions, location in various architectures or other locations, or various activity goals. Such activities can involve educational pursuits, vocational activities, sports events, or other varied activities.

The human bio-info/data can also include other aspects besides that which is physiologically related such as location data. Location data can be matched with location of other humans or location of various occurrences of activity in which performance or habit patterns of an individual can be assessed. For instance, performance or habit patterns related to parenting can be determined such as how much time is spent with a child regarding certain activities. These activities can include eating, educational events, sports or entertainment events, etc. This human-bio info/data can then be analyzed statistically or otherwise to determine rankings or other assessments related to parenting.

Other human bio-info/data can include recorded observations by one or more individual humans regarding preferences or dislikes associated with activities, habits, food choices, associations, better aspects associated with one or more individual humans etc. For instance, an individual may express a desire to be like another individual in terms of physical fitness, general overall appearance, mental acuity, or other such admirable traits. The human bio-info/data as recorded observations can be used real-time or later on to assist in food selection for the individual. These recorded observations can be also incorporated into other goals such as having diet constraints, physiological requirements, etc. These observations can also be directed to other humans such as a parent desiring their child to eat in a certain manner or to have certain food items or to avoid other food items. These observations can then be used for determining what food to provide to the child in certain instances such as at school or a sporting event. Observations obtained from the child as to likes and dislikes and observations obtained from the parent as to health, physiological, illness management, and other parental goals can then be combined to determine or optimize various choices available. This approach can allow for implementation of desires and goals of both parent and child in a peaceable manner.

Other human bio-info/data can include activity parameters involving measurement of quality or quality of various activities performed. For instance, these activities could include instructional activities at school having to do with concentration levels, amount of involvement, degree of insight and expression, work capacity, interest level, level a distraction, ingenuity, leadership, and other factors related to a learning environment. These sorts of factors can also be measured or otherwise observed as human bio-info/data in other environments such as a workplace, a home environment, an entertainment environment, or other such environments or locations. For instance in a home environment, bio-info/data could be related to communication levels, cooperation levels, interest levels, selfishness levels, etc. of one or more household members either individually or collectively. Information or data content can be extracted from visual, audio, location, or other data to various recognition schemes, statistical analysis, etc. Behavioral profiles can be then establish their individual members or collection of members and compared with normative standards. These sorts of determinations can also be applicable to other environments such as workplace, entertainment, etc.

Various human bio-info/data devices can be set up in a local or wide area network anywhere within a particular architectural structure or across the Internet. By networking the human bio-info/data devices together they can be working in a synergistic approach in which human bio-info/data collected by one device can be shared with other devices so that complementary human bio-info/data can be collected by the various device members of the networked team of devices. This arrangement can be conducive for such desires is testing hypotheses in which human bio-info/data collected by a set of one or more first devices can then be fed and with other bio-info/data collected by us set of one or more second devices. For instance, human bio-info/data devices could be located in refrigerators, food fabricators or printers, stoves, microwave ovens, conventional ovens, convection ovens, cook tops, sinks, dishwashers, wearable devices, food utensils, eating area furniture, kitchen sinks, bathroom equipment including sinks, showers, bathtubs, and toilets, and other structures, equipment, etc. related to an individual's living environments such as office furniture, bedroom furniture, etc.

Human bio-info/data devices can include Google glasses, smart watches, mobile devices such as iPhone, smart phones, handsets, Android phones, tablets, phablets, laptops, personal devices, smart earpieces, electronically enabled clothing, made by Apple, Samsung, Google, etc. Human-info/data devices can be formed as non-reconfigurable hardware devices or can be programmable devices to receive programming related to human bio-info/data functionality. Functionality can also be incorporated into operating systems such as Android OS or the Apple OS. Other form factors can include sports equipment and other such athletic gear. For instance, skis with various sensors to determine quantity and quality of athletic output by a skier over a course of a day or season could be used as another sort of bio-info/data device. Another example could include sensors integrated with bicycles, hiking gear, sports balls, and other athletic equipment. What are more of these human bio-info/databases can be branded under various corporate marketing or other programs which furnish one or more portions of generic or hardware specific programming or other instruction sets related to functionality in collecting or analyzing bio-info/data such as through food suppliers, big-data analytics, food fabricator system providers, or device makers. Branding can include subscription services to information such as updated recipes, lifestyle adjustment, or other aspects related to quantified life interests, etc.

Human bio-info/data devices can include sophisticated data collection instruments such as nuclear magnetic resonance equipment including NMR rings to determine such as molecular markers. Human bio-info/data devices can be used to collect other quantified-self information and data to be used in turn by human food fabricators, big-data analytics, and human food supply systems. For instance, human bio-info/data can be collected regarding home life including dialogue between spouses, parents and children, siblings, other relatives, visitors, guests, etc. Dialogue can be analyzed for emotional, intellectual, psychological, physiological, behavioral, normative, aberrant, and other content, etc., assessing performance relative to peers, normative behavior, outside of normative behavior, spouse, other norms, children relative to other children, relative to other parents, etc. Scenarios can include percentage of emotionally heated dialogue to train parents and children relative to norms or other statistical patterns, whether homework atmosphere is conducive for substantive production, accounting and other financial data associated with household expenditures, stress levels, health levels, etc., driving habits as recorded by vehicle instrumentation, quantity, quality, scheduling, etc. of exercise regimens, etc. Quantified-self or human bio-info/data measurements and information can also be used to identify interests, desires, or dislikes regarding activities, environments are other aspects mentioned herein using quantified scoring or other reporting techniques. Other scenarios can include assessing reading level and suggesting appropriate materials to be read. Other reading data could include number of words read to children on a daily, weekly, monthly, annual, etc. basis.

Human bio-info/data or quantified-self data can tie performance levels with ingestion of food and other materials. For instance, ingestion of various sugars such as fructose, dextrose, sucrose, or other combinations thereof can affect ability to lose adipose tissue, maintain energy and endurance levels, and other factors of performance including intellectual performance and work-product production. Types of fats included in the diet such as amount of omega-three, omega-six, and the ratios thereof and also including DHA, EPA, trans-fats, or arachadonic acid, saturated fats, polyunsaturated fats, monounsaturated fats, or other fats can also affect performance levels including intellectual ability. Various contaminants such as lectins, and phytic acid as found in grains, beans, seeds, nuts, tubers, etc. can detrimentally affect mineral absorption along with other biochemical activities further impacting performance and health levels. Protein quality including issues related to denaturization of amino acids can affect absorbability and digestion efficacy. These and other factors can be tracked as bio-info/data and integrated into systems using bio-info/data devices, food fabricators, egg-data analytics, and food supplier systems to assist users with optimizing goals and performance levels.

Human bio-info/data regarding educational environments can include how many times did a child speak to a teacher, activity levels for various endeavors such as athletics, classroom participation, extracurricular activities, study hall, etc. Bio-info/data regarding educational environments can include other quantified-self info/data such as amount of bullying experienced, amount of positive social interaction with other students during a school week, amount and type of food eaten during lunchtime, and comparisons of this and other data with statistical groupings such as averages, means, etc. such as locally, regionally, nationally, etc.

Quantified-self info/data as human bio-info/data can include that involving self-improvement, efficiency, or other measurements in various environments requiring performance such as workplace, home, athletics, education, etc. Quantity and quality of work-product through use of text-based, speech-based, pattern recognition, brainwave pattern tracking, measurement sensors attached to equipment, and other instruments such as musical instruments, etc. or other sorts of analysis can be implemented. Efficiency measures can be used to track duration, time on task, output level profiles, rest break profiles, etc. For instance, measures such as time using twitter, typing, talking on phone, etc. can be compared with other activities. These efficiency measures and other data can be related to degree of difficulty of the task at hand. Other bio-info/data can include measurements related to habits or traits targeted for acquisition, improvement, decrease, or elimination. Such habits or traits can relate to diet, physical exercise, skill practice sessions including intellectual, physical, musical, artistic, athletic, social, communication, educational, governmental, and other skills. Objective measures related to work and include time spent consuming recreational media, time spent on social networks, time spent on personal phone, etc. and can be compared to coworkers or expectation by company managers and graphical display of comparisons or issues flagged about level of engagement with work compared with thresholds. Other quantified-self or bio-info/data can include other objective measures of activities related to life including trips outside the home, meal and snack patterns, social contacts, activity patterns, etc. as compared to specified others or standardized norms. Results can be displayed changes can be recommended based on goals, therapies, norms, etc., such as for instance, recommendations of more trips for depressed individuals, less eating for the abuse, more social contacts for those with few social contacts, alerts regarding activity levels indicating possible individual addiction, etc.

Quantified-self info/data or otherwise human bio-info/data can be linked with systems such as big-data analytics or personal analytics in various user interfaces including visual, audio, tactile, and other such user interfaces to provide feedback, incentives, and further encouragement in behavioral modification on an individual, group, corporate, or other basis. Users or others can identify which types of information or data should be tracked, assessed, or otherwise processed. For instance, users may specify desires to be more effective in interacting with others, gaining experiences, skills, production goals, etc. Such systems can be directed for manipulation of behavior associated with diet such as increasing or decreasing intake of various foods, adopting habit patterns involving exercise duration, quantity, quality, type, etc., associating with other individuals or groups with common goals or desires, etc. adopting or shunning various mannerisms and expression such as volume level, word choice, content of speech, signals of irritation, abrasive content, or other methods of expression. Computer use can be tracked as well regarding type of use, duration, rest breaks, etc. Quality of family life such as time spent together in various activities. Personality traits of individuals and groups can also be identified through statistical and other analysis of such data to be used for planning and other purposes.

Human bio-info/data or otherwise quantified-self info/data can include shopping activities related to food acquisition, exposure to toxins, dietary goals such as amount of desired food items to be ingested over a period of time, recording itinerary or other travel routes taken between or within stores such as grocery stores, department stores, discount stores, etc., or shopping through other means such as Internet-based purchasing on various websites. Collection of such information can also be further encouraged through discounting cost of various items or other incentives.

Human bio-info/data or quantified-self info/data can be used to acquire objective measurements and other assessments related to the various activities of parenting. For instance, regarding tummy time, theories include that infants should be spending a certain amount of time every day on their stomach for instance 30 minutes a day or as recommended by a physician. A system integrated with such human bio-info data could provide three user interfaces various alerts and other parenting information for instance, if tummy time is below recommended thresholds. Measurements regarding the spoken word from parents can be used to alert, train, or otherwise inform parents of their performance levels. Infants or small children could be assigned target words that parents are to speak to a child at certain times or throughout the day. Such performance can be them monitored such as through daily, local, national averages are other statistical measures to assess relative performance levels.

Quantified-self bio-info/data for parenting and other activities can also include measurements related to book reading such as particular types, subject areas, quantity, quality, amount of time spent on a daily, weekly, monthly, etc. basis, reading level for grade or age with comparisons regarding such measures statistically or otherwise on various local to national, etc. levels. Another measurement can include amount of eye contact through neurotypical metrics or neurotypical eye contacts. Such human bio-info/databases as Google glasses, or other glasses that can measure eye contact can be used, or other devices such as facial analyzers can be used as human bio-info/data devices. Feedback can be provided to users with a variety of intelligence levels to increase cooperation among themselves or for other training purposes.

Other parenting applications for quantified-self info/data or otherwise human bio-info/data can involve monitor, screen, television, movie, or other media displays. For instance, parental goals could include limiting amounts at which their children spend such time. Various parental controls can also involve content monitoring, encrypted logging of activity, content ratings for objectionable material including levels, degrees, intensity, etc. of violence, pornography, vulgarity, wantonness, shock effect, social aberration, instilling of fear, etc. Other factors can include viewing location in relation to proximity of display, etc.

Human bio-info/data can also include metrics related to sleep quantity, quality, etc. These measurements can be compared with various norms to ascertain, classify, etc. sleep patterns for children. For instance, a child starts to get sleepy at 7 PM and has a period of light sleep around 11 PM. Through use of a system integrated such as with big-data analytics and human bio-info data this and other behavior can be compared or classified to inform parents of any concerns to be noted. Insights derived from this analysis can also be used to tailor calendars or otherwise schedule activities of the children based on their particular sleep-wake patterns occur throughout the day and night rather than merely relying on expected norms of behavior. This tailoring approach could also be applied directly with educational institutions such as advanced or progressive grade school or higher levels schools.

Parental use of human bio-info data can also include potty training where parents can track toileting successes of their children over a period of time. Such success training can be used for motivational purposes for the children or to provide feedback to the parents regarding their skills in training their children. Objective measures of success can include amount of accidents over a period of time with a trend toward gradual reduction indicating success. Comparison with training profiles of other children can help parents determine if there are concerns to be had.

Analysis of parenting performance can further include comparison of objective measures involving other parents similarly situated regarding location such as city, state, nation, etc., parental lifestyle including whether both spouses work outside the home, amount and type of social network friends, rankings regarding top ten percent or top quartile, etc. Further comparisons include objective measurements those of others same school, citywide, statewide, nationwide, worldwide, social network-wide with analysis or other outcomes reported to parents, teachers, others in authority, etc. and can include such as recommendations for suitable responses.

The animal bio-info/data device (wearable) 120 can include the following. The animal bio-info/data device (wearable) 120 can collect biological and other data non-invasively, invasively, other sample collection, etc. regarding animal device wearer such as regarding physiological status involving molecular, chemical, analytes, electrolytes, cellular, tissue, organ, systems (e.g., skeletal, muscular, immune, lymphatic, cardiovascular, urinary, digestive, respiratory, nervous, endocrine, reproductive, integumentary, etc.), functional (e.g., sleeping, eating, ambulating, non-ambulatory postures, emitting sounds, listening, seeing, eliminating, reacting, location, etc.), electrical, disease (e.g., past, present, potential, etc.), mechanical (structural, movement, etc.), and other related status.

The animal bio-info/data device (wearable) 120 can be worn on animal by collar, vest, strap, mask, blinder, blanket, harness, piercing, branding, hood, shoeing, tagging, clothing, band, belt, etc.

The animal bio-info/data device (wearable) 120 can communicate with human owner, manager, attendant, other animal bio-info/data devices (e.g., wearable or non-wearable), feed fabricator, big-data analytics system, food ingredient supplier, etc.

The animal bio-info/data device (wearable) 120 can include for example subscription services (health, food, cooking, etc.) sell device and applications thru home or kiosk food fabricator networks, device and applications sold by manufacturers of food fabricator or medical-health-sports providers-equipment manufacturers (e.g., 3D Systems, Natural Machines, Cargill, Massey Ferguson, John Deere, livestock or pet veterinary clinics or pet feed stores, General Electric, Polar, Nintendo, Samsung, etc.).

The animal bio-info/data device (non-wearable) 124 can include the following. The animal bio-info/data device (non-wearable) 124 can collect biological and other data non-invasively, invasively, other sample collection, etc. regarding one or more associated animals such as regarding physiological status involving molecular, chemical, analytes, electrolytes, cellular, tissue, organ, systems (e.g., skeletal, muscular, immune, lymphatic, cardiovascular, urinary, digestive, respiratory, nervous, endocrine, reproductive, integumentary, etc.), functional (e.g., sleeping, eating, ambulating, non-ambulatory postures, emitting sounds, listening, seeing, eliminating, reacting, location, etc.), electrical, disease (e.g., past, present, potential, etc.), mechanical (structural, movement, etc.), and other related status.

The animal bio-info/data device (non-wearable) 124 can be part of an enclosure, fence, barn, pen, etc. located in proximity of animal (e.g., structural member, fixture, accessory, gate component, etc.), or adjacent or occasionally in contact (e.g., stall, trough, chute, floor, trailer, cage, water container, sewage system, etc.).

The animal bio-info/data device (non-wearable) 124 can communicate with human owner, manager, attendant, other human bio-info/data devices (e.g., wearable or non-wearable), food fabricator, big-data analytics system, food ingredient supplier, etc.

The animal bio-info/data device (non-wearable) 124 can for example subscription services (livestock management, pet care, etc.) sell device and applications thru farm, home, or kiosk feed fabricator networks, device and applications sold by manufacturers of feed fabricator, or veterinary-health-production management providers-manufacturers (e.g., 3D Systems, Natural Machines, Cargill, Massey Ferguson, John Deere, livestock or pet veterinary clinics or pet feed stores, General Electric, Polar, Nintendo, Samsung, etc.).

Further aspects regarding the wearable and non-wearable animal bio-info/data devices can include collecting information or data related to feed preferences of the animals such as texture, color, or taste such as sweet, sour, salty, or other taste sensations. Such collected information or data can in a sense profile a particular individual animal as far as how the individual animal reacts to various foods and other indigestible materials from a psychological, physiological, sensory, or other aspects. This type of profiling can then be used in order to tailor the various food and other indigestible materials for the individual animal. For instance, the profiling information can be used to tune macronutrient, micronutrient, bacterial or other content of feed in real time regarding various activity levels of the individual animal. These activity levels can be related to environmental conditions such as weather conditions, location in various architectures, such as barns or pens, or other locations, or various activity goals. Such activities can involve grazing in pasture, being controlled in pens, involving slaughter time regarding the fat or protein content, or other activities requiring more or less energy levels of the individual animal.

The bio-info/data can also include other aspects besides that which is physiologically related such as location data. Location data can be matched with location of other humans or location of various occurrences of activity in which performance or habit patterns of an individual can be assessed. For instance, performance or habit patterns related to parenting can be determined such as how much time is spent with a child regarding certain activities. These activities can include eating, educational events, sports or entertainment events, etc.

The human food fabricator 128 can include the following. The human food fabricator 128 can produce food and other edible materials such as bacteria through such as assembly, printing, sputtering, ablation, deposition, spraying, injection, mixing, combining, hydrating, dehydrating, applying energy, removing energy, etc. and other functional aspects from instructions pertaining to bio-info/data collected, big-data analytics, instructions received, exemplars referenced.

The human food fabricator 128 can send instructions and other information to human bio-info/data devices to collect bio-info/data based on testing protocols, hypothesis testing, user, service-provider, or organization inquiry or direction.

The human food fabricator 128 can receive instructions from user, service-provider, organization, big-data/info analytics system with reference to past, present, and/or anticipated requirements for edible materials as related to expressed desires and/or bio-info/data received from bio-info/data devices.

The human food fabricator 128 can be incorporated into such as kitchen, break room, vending area, restaurant, mobile platform, etc. as small counter-top unit or large kiosk unit.

The human food fabricator 128 can communicate with human, bio-info/data devices (e.g., wearable or non-wearable), food fabricator, big-data analytics system, food ingredient supplier, etc.

The human food fabricator 128 can include for example subscription services (health, food, cooking, etc.) sell fabricator and applications thereof thru consumer and commercial markets, fabricator manufacturers, or medical-health-sports providers-manufacturers (e.g., 3D Systems, Natural Machines, Whirlpool, KitchenAid, Miele, medical or health clinics, General Electric, Polar, Nintendo, Samsung, etc.).

Human food fabricator can be used independently or in combination with communicating with human bio-info/data devices, big-data analytics, or human food supply systems to test hypotheses regarding combination of ingredients that may solve a problem, induce a condition, relieve a symptom, or otherwise achieve an expressed or unexpressed goal. Hypotheses testing can be achieved through adjustment of various ingredient levels of food or other ingested materials over a period of time sufficient to produce a variety of samples having different combinations of the varying ingredients.

Human food fabricator can be used to determine what food or other ingested material to provide to the user based upon received human bio-info/data, direction or information from big-data analytics, or information or data from human food supply system. By doing so, it may be possible for the human food fabricator to provide desired materials to the user without the user having to input much or any explicit information to the human food fabricator.

Human food fabricator can be formed to include non-reconfigurable hardware or can be programmable to receive programming related to human food fabrication functionality. Such functionality can also be incorporated into operating systems such as Android OS or Apple OS.

Human food fabricators can be communicatively linked to human bio-info/data devices to collect status from humans before they human food fabricators are used for instance as utilized in pre-production staging. As an example, as a user approaches a human food fabricator, one or more human bio-info/data devices worn by the user can communicate to the human food fabricator various bio-info/data status such as blood sugar levels, last time food or beverage was consumed, past or planned activity levels, hormone levels, etc. to provide additional context in determining optimal production of food and other ingested materials to provide to the user.

Kiosk-style dispensing machines having relatively small footprint ranging in size such as countertop units to larger floor model vending machines can incorporate human food fabricators and other communication systems linked to human bio-info/data devices, big-data analytics, and human food supply systems. Kiosk-style dispensing machines can include aspects of the human food fabricators as well as further communication and bio-info/data functionality to provide fuller service regarding selection and purchasing options for users. Kiosk-style dispensing machines as network together can provide overall bio-info/data collection for a user or group of users for such functions as tracking participation in various activities and events. For instance, as further described below kiosk-style dispensing machines can be located at educational, business, entertainment, shopping, institutional, and other locations for activities in advance such that use of the kiosk-dispensing machines will indicate participation by the users in certain activities and events related to these locations. Food chains such as McDonald's or Burger King, or other food distribution chains, or vending chains such as Red Box or Coinstar could locate kiosk-style dispensing machines in numerous varied locations some of which are depicted in FIG. 1-K to include location such as marketplaces, sports arenas, theaters, schools, office buildings, and hospitals. Other locations are depicted in FIG. 1-N to include sidewalks, public parks, restaurants, public buildings, air-travel facilities, and food courts. These locations are exemplary so or not limiting as far as other possibilities for positioning kiosk-style dispensing machines.

For instance, on aircraft of an airline, passengers may send quantified-self bio-info/data to communication system located on the plane integrated with one or more kiosk-style dispensing machines containing food fabricators. Such quantified-self bio-info/data can then be used by the fabricators on the aircraft to be Incorporated in production or otherwise dispensing of food and other ingested materials as tailored to the passenger requirements and desires. For instance, passengers would particular health requirements such as levels of salt, sugar, mineral, fat, protein, carbohydrate, micronutrients, macronutrients, etc. can receive tailored food and other ingested materials accordingly. Status of other passengers such as stress levels, hunger levels, past, present, or future activities, etc. can also be used to formulate tailored food and other ingested materials for the passengers. In certain circumstances enough information and data can be collected by fabricator systems on the plane so that it may be possible for the passengers to receive food or other ingested materials without having to directly communicate with airline attendants yet the passengers can receive what they require or desire.

Travel facilities could include airports, train stations, bus stations, ocean liner ports, transit stations, and other facilities. Kiosk-style dispensing machines could also be located on the vehicles themselves including airplanes, trains, buses, ocean liners, transit vehicles, and other vehicles, etc.

Kiosk-style dispensing machines can combine fabricator aspects with being a waypoint for big-data analytics, food supplier systems, and bio-info/data quantified-self data acquisition in order to receive quantified-self bio-info/data, analytics, and supply information to assist in determining various food and other ingested materials to produce, arrange or otherwise furnish. Kiosk-style dispensing machines can also provide production or other use data to human bio-info/data devices, big-data analytics, or food supply systems for their use and analysis. For instance, kiosk-style dispensing machines having received bio-info/data indicating that the user has a certain health condition may note in the user's record that the kiosk-style dispensing machine provided food or other ingested materials in compliance with were not in compliance with recommendations for such health condition.

For instance, large food chains such as McDonald's or Burger King could use kiosk-style dispensing machines to collect quantified-self bio-info/data in the process of fabricating or otherwise providing food and ingested materials through the branded kiosk-style dispensing machines. The quantified-self bio-info/data could involve health, physiology, lifestyle, family life, occupational data, educational data, etc. of the one or more users. Such information and data can then be fed into the food chain network, big-data analytics, supply chain systems, information vendors, health systems, etc. Analytics could be analyzing such information and data, for instance, such as frequency of visits, amount of time spent with others such as children and parents in locations of kiosk-style dispensing machines, participation in activities and events such as sports, movies, recreational parks, educational center such as libraries, etc. Kiosk-style dispensing machines in this and other approaches can then be viewed as related to family lifestyle, occupational pursuits, entertainment and recreational interests, and other areas. Kiosk-style dispensing machines located in educational institutions such as schools could afford students a wide variety of selection of food and other ingested materials as provided with constraints and other factors related to interests of the students and those related such as parents, health providers, educators, school board members, etc. Kiosk-style dispensing machines could be integrated with other facilities, locations, event centers, activity areas, etc. to help track user or customer activity. For instance, kiosk-style dispensing machines could be tied in with social networks or other social networking systems as related to comments of others such as friends, relatives, observers, and others accessing the social networks or other social networking systems. With this and other approaches kiosk-style dispensing machines and their networks thereof and other systems and networks can be used in a universe of overlapping functionality and collection of data and information through word analysis, comment recognition. For instance comments from friends can be quantified as quantified-self bio-info/data, for instance, on how well a person is doing in a particular area of pursuit such as improvement in health, sociability, educational pursuits, social presence, occupational goals, etc. including positive improvement or setbacks.

The animal feed fabricator 132 can include the following. The animal feed fabricator 132 can produce feed and other edible materials such as bacteria through such as assembly, printing, sputtering, ablation, deposition, spraying, injection, mixing, combining, hydrating, dehydrating, applying energy, removing energy, etc. and other functional aspects from instructions pertaining to bio-info/data collected, big-data analytics, instructions received, exemplars referenced.

The animal feed fabricator 132 can send instructions and other information to animal bio-info/data devices to collect bio-info/data based on testing protocols, hypothesis testing, user, service-provider, or organization inquiry or direction.

The animal feed fabricator 132 can receive and generate instructions for edible material production from user, service-provider, organization, big-data/info analytics system with reference to past, present, and/or anticipated requirements for edible materials as related to expressed desires and/or bio-info/data received from bio-info/data devices.

The animal feed fabricator 132 can be incorporated into such as feed areas, pens, troughs, barns, stalls, feed assemblies, home units sized for requirement of small or large animals.

The animal feed fabricator 132 can communicate with human, bio-info/data devices (e.g., wearable or non-wearable), big-info/data analytics system, feed ingredient supplier, etc.

The animal feed fabricator 132 can include for example subscription services (livestock management, pet care, etc.) sell fabricator and applications thru farm, home, or kiosk feed fabricator networks, device and applications sold by manufacturers of feed fabricator, or veterinary-health-production management providers-manufacturers (e.g., 3D Systems, Natural Machines, Cargill, Massey Ferguson, John Deere, livestock or pet veterinary clinics or pet feed stores, General Electric, Polar, Nintendo, Samsung, etc.).

Animal feed fabricator can be used independently or in combination with communicating with animal bio-info/data devices, big-data analytics, or animal feed supply systems to test hypotheses regarding combination of ingredients that may solve a problem, induce a condition, relieve a symptom, or otherwise achieve an expressed or unexpressed goal. Hypotheses testing can be achieved through adjustment of various ingredient levels of feed or other ingested materials over a period of time sufficient to produce a variety of samples having different combinations of the varying ingredients.

Animal feed fabricator can be used to determine what feed or other ingested material to provide to an animal based upon received animal bio-info/data, direction or information from big-data analytics, or information or data from animal food supply system. By doing so, it may be possible for the animal food fabricator to provide desired materials to the animal with little or no intervention required by human. Animal feed fabricators can take the form of feed printers or can take other forms such as assemblers, combiners, mixers, etc. Feed furnished by animal feed fabricators can be tailored toward either pet markets such as PetSmart or livestock involved with agribusiness industries such as ConAgra. In either case, the feed can be tailored by the animal feed fabricator regarding micronutrients, macronutrients, bacterial content, and other ingredients for goals such as activity levels in which the animal is to his stay in a stationary position for lengthy periods of time, or is to be fully animated, for instance, in order to transport itself from one location to another.

The big-info/data analytics system 136 can include the following. The big-info/data analytics system 136 can receive analysis instructions from user, service-provider, organization, bio-data/info devices, fabricators with reference to past, present, and/or anticipated requirements for edible materials as related to expressed desires and/or bio-info/data received from bio-info/data devices.

The big-info/data analytics system 136 can run statistical, probabilistic, or other models on bio-info/data collected by bio-info/data device(s) and expressed desires with reference to past, present, and/or anticipated edible materials requirements to determine patterns, options, or other desirable outcomes for instructing production of material by fabricator(s) or further collection of bio-info/data by device(s).

The big-info/data analytics system 136 can send instructions and other information to human or animal bio-info/data devices to collect bio-info/data based on testing protocols, hypothesis testing, user, service-provider, or organization inquiry or direction, and results of analytics system analysis.

The big-info/data analytics system 136 can communicate with humans, bio-info/data devices, fabricators, food ingredient suppliers, feed ingredient suppliers, etc.

The big-info/data analytics system 136 can include for example subscription services (per human or animal interests) sell cloud-based analysis time, application downloads, etc. thru consumer and commercial markets, device and/or fabricator manufacturers, or medical-health-sports-veterinary-pet providers or equipment manufacturers (e.g., 3D Systems, Natural Machines, Whirlpool, KitchenAid, Miele, medical or health clinics, General Electric, Polar, Nintendo, Samsung, Cargill, Massey Ferguson, John Deere, livestock or pet veterinary clinics or pet feed stores, etc.).

Big-data analytics such as for special-purpose as provided by such companies as IBM, Microsoft, Amazon, SAP, Oracle, cloud services, Apple, Google, Accenture, Twitter, Facebook, etc. can be used to drive communication with human or animal bio-info/data devices, human or animal food or feed fabricators, human or animal food or feed supply systems, etc. to test hypotheses regarding combination of ingredients that may solve a problem, induce a condition, relieve a symptom, or otherwise achieve an expressed or unexpressed goal. Hypotheses testing can be achieved through adjustment of various ingredient levels of food, feed or other ingested materials over a period of time sufficient to produce a variety of samples having different combinations of the varying ingredients.

Big-data analytics can be used to conduct experiments to see the effects of various food or other ingested materials or combinations thereof upon users. For instance, direction can be sent from big-data analytics to a human food fabricator or an animal food fabricator to dispense particular kinds of food or feed materials based upon a subjects behavioral profile such as including the extent of exercise, sleep quality, plan performance levels, etc. Parameters regarding materials to be dispensed can be varied in order for big-data analytics to assess statistically significant correlations, spikes in probability distributions, etc. Studies on various populations can also be performed to identify similarities or differences related to lifestyle factors found with impacts on health, workplace performance, education levels, economic output, social integrity, and other outcomes. Big-data analytics can be tied in with social networks for further analysis and distribution of outcomes.

Statistical and other analysis can be performed on other aspects including parenting such as duration of time spent with children in relation to eating, teaching, playing, overseeing, chauffeuring, taking trips, etc. Proximity data based on location can be used for some of this analysis.

Big-data analytics can also be directly tied through communication links to human food supply systems or animal feed supply systems to send information and data backup the supply chain. For instance, big-data analytics through various analysis could determine trends in health or sickness and possibly identify sources for such. This analysis could then be fed back up through the various supply chains to alert those in positions of responsibility.

Human food ingredient supplier system 142 can include the following. Human food ingredient supplier system 142 can receive ordering instructions, bio-info/data, ingredient use information, etc. from user, service-provider, organization, bio-data/info devices, fabricators, big-info/data analytics, etc. with reference to past, present, and/or anticipated requirements for edible materials as related to expressed desires and/or bio-info/data received from bio-info/data devices.

Human food ingredient supplier system 142 can perform supply or other analysis models on bio-info/data collected by bio-info/data device(s) and expressed desires with reference to past, present, and/or anticipated edible materials requirements to determine patterns of consumption, projected demand, for instructing stocking, shipment, or other supply chain functions.

Human food ingredient supplier system 142 can send instructions and other information to bio-info/data devices to collect bio-info/data based on testing protocols, hypothesis testing, user, service-provider, or organization inquiry or direction, and results of supply chain model analysis.

Human food ingredient supplier system 142 can be incorporated either by separate or common structures with bio-info/data devices, fabricators, or more central, separate entities such as server-based or cloud-based implementations.

Human food ingredient supplier system 142 can communicate with humans, bio-info/data devices, fabricators, big-info/data analytics, etc.

Human food ingredient supplier system 142 can include for example subscription services (per human interests) sell cloud-based analysis time, application downloads, etc. thru commercial markets, device and/or fabricator manufacturers, or medical-health-sports-veterinary-pet providers or equipment manufacturers (e.g., 3D Systems, Natural Machines, Whirlpool, KitchenAid, Miele, medical or health clinics, General Electric, Polar, Nintendo, Samsung, etc.).

Human food supply systems can be communicatively linked to big-data analytics to receive information and instruction related to analysis performed on human food and other materials thereby supplied. Sending information and instruction based upon this analysis up the supply chain can be beneficial to those in positions of responsibility for instance, in cases where outbreaks of illness have occurred. Other sorts of analysis can include information related to improvement in health in various subjects using food or other ingested materials. Trends in shopping or preferences in selection can also be identified and supplied to the human food supply systems. The human food supply systems cannot only provide food ingredients and other materials to the human food fabricators but can also furnish ready-made food items to be delivered through commercial channels such as UPS, FedEx, U.S. Postal Service, etc. Such human food supply systems could include Amazon, Amazon Fresh, Walmart outlets, Costco outlets, or other such conglomerates with various other distribution channels such as Nestlé, Unilever, General Mills, McDonald's, Coca-Cola, PepsiCo, or other big-food conglomerates, etc. see having broad families of food and other ingested materials, etc. such as possibly to institutions as hospitals, schools, prisons, etc.

Human bio-info/data, fabricator information, big-data analytics, and human food supply system information can be used by human food supply systems for delivery analysis, planning, execution, etc., providing recommendation to users, assessing information to collect from customers, determination of advertising targeting, etc.

Animal feed ingredient supplier system 146 can include the following. Animal feed ingredient supplier system 146 can receive ordering instructions, bio-info/data, ingredient use information, etc. from user, service-provider, organization, bio-data/info devices, fabricators, big-info/data analytics, etc. with reference to past, present, and/or anticipated requirements for edible materials as related to expressed desires and/or bio-info/data received from bio-info/data devices.

Animal feed ingredient supplier system 146 can perform supply or other analysis models on bio-info/data collected by bio-info/data device(s) and expressed desires with reference to past, present, and/or anticipated edible materials requirements to determine patterns of consumption, projected demand, for instructing stocking, shipment, or other supply chain functions.

Animal feed ingredient supplier system 146 can send instructions and other information to bio-info/data devices to collect bio-info/data based on testing protocols, hypothesis testing, user, service-provider, or organization inquiry or direction, and results of supply chain model analysis.

Animal feed ingredient supplier system 146 can be incorporated either by separate or common structures with bio-info/data devices, fabricators, or more central, separate entities such as server-based or cloud-based implementations.

Animal feed ingredient supplier system 146 can communicate with humans, bio-info/data devices, fabricators, big-info/data analytics, etc.

Animal feed ingredient supplier system 146 can include for example subscription services (per animal interests) sell cloud-based analysis time, application downloads, etc. thru commercial markets, device and/or fabricator manufacturers, or veterinary-pet providers or equipment manufacturers (e.g., 3D Systems, Natural Machines, General Electric, Polar, Nintendo, Samsung, Cargill, Massey Ferguson, John Deere, ConAgra, livestock or pet veterinary clinics or animal/pet feed stores, etc.).

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

To the extent that formal outline headings are present in this application, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, any use of formal outline headings in this application is for presentation purposes, and is not intended to be in any way limiting.

Throughout this application, examples and lists are given, with parentheses, the abbreviation "e.g.," or both. Unless explicitly otherwise stated, these examples and lists are merely exemplary and are non-exhaustive. In most cases, it would be prohibitive to list every example and every combination. Thus, smaller, illustrative lists and examples are used, with focus on imparting understanding of the claim terms rather than limiting the scope of such terms.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although one or more users maybe shown and/or described herein, e.g., in FIG. 1, and other places, as a single illustrated figure, those skilled in the art will appreciate that one or more users may be representative of one or more human users, robotic users (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g., "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

Throughout this application, the terms "in an embodiment," "in one embodiment," "in some embodiments," "in several embodiments," "in at least one embodiment," "in various embodiments," and the like, may be used. Each of these terms, and all such similar terms should be construed as "in at least one embodiment, and possibly but not necessarily all embodiments," unless explicitly stated otherwise. Specifically, unless explicitly stated otherwise, the intent of phrases like these is to provide non-exclusive and non-limiting examples of implementations of the invention. The mere statement that one, some, or may embodiments include one or more things or have one or more features, does not imply that all embodiments include one or more things or have one or more features, but also does not imply that such embodiments must exist. It is a mere indicator of an example and should not be interpreted otherwise, unless explicitly stated as such.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

What is claimed is:

1. A computationally-implemented method, comprising:
    electronically receiving user biological status information from electronically involved detection of one or more biological user conditions;
    electronically obtaining one or more user ingestion preference indications; and
    electronically providing instruction to electronically direct at least in part one or more factors of electronically controlled dispensing of manually administrable orally ingestible material based upon the electronically receiving user biological status information from electronically involved detection of one or more biological user conditions and based upon the electronically obtaining one or more user ingestion preference indications;
    electronically accessing record data associated with ingestible material dispensing by one or more dispensing machines to one or more individuals;
    electronically accessing record data associated with one or more biological user conditions of the one or more individuals collected by the one or more dispensing machines;
    electronically reporting regarding one or more relationships between the record data associated with the ingestible material dispensing by the one or more dispensing machines to the one or more individuals and the record data associated with the one or more biological user conditions of the one or more individuals collected by the one or more dispensing machines;
    electronically performing electronic-semiconductor-transistor-based-device-assisted monitoring of user physiological aspect data of an electronic-semiconductor-transistor-based-device user involving in part orchestration of electronic-semiconductor-transistor-based voltage levels and performing electronic-semiconductor-transistor-based-device-assisted monitoring of user behavioral aspect data of the electronic-semiconductor-transistor-based-device user involving in part orchestration of electronic-semiconductor-transistor-based voltage levels;
    electronically performing electronic-semiconductor-transistor-based-device-assisted reception of food-based ingredient information from one or more food-based ingredient information resources involving in part orchestration of electronic-semiconductor-transistor-based voltage levels;
    electronically performing electronic-semiconductor-transistor-based-device-assisted transmission of food-based fabricator operational indication to one or more food fabricator machines involving in part orchestration of electronic-semiconductor-transistor-based voltage levels based at least in part on the electronically performing electronic-semiconductor-transistor-based-device-assisted monitoring of user physiological aspect data of an electronic-semiconductor-transistor-based-device user involving in part orchestrated manipulation of electronic-semiconductor-transistor-based voltage levels and performing electronic-semiconductor-transistor-based-device-assisted monitoring of user behavioral aspect data of the electronic-semiconductor-transistor-based-device user involving in part orchestration of electronic-semiconductor-transistor-based voltage levels and based at least in part on the electronically performing electronic-semiconductor-transistor-based-device-assisted reception of food-based fabricator information involving in part orchestration of electronic-semiconductor-transistor-based voltage levels;
    electronically outputting electronic-semiconductor-transistor-voltage-level-based-state-machine-assisted-user-menu-selection display associated with electronic-semiconductor-transistor-voltage-level-based-state-machine-assisted collection of user-physiological information, associated with electronic-semiconductor-transistor-voltage-level-based-state-machine-assisted collection of user-conduct information, and associated with electronic-semiconductor-transistor-voltage-level-based-state-machine-assisted obtaining of food-based information;
    electronically receiving electronic-semiconductor-transistor-voltage-level-based-state-machine-assisted reception of user-menu-selection display-choice data associated with electronic-semiconductor-transistor-voltage-level-based-state-machine-assisted collection of user-physiological information, associated with electronic-semiconductor-transistor-voltage-level-based-state-machine-assisted collection of user-conduct information, and associated with electronic-semiconductor-transistor-level-level-based-state-machine-assisted obtaining of food-based information;
    electronically formulating electronic-semiconductor-transistor-voltage-level-based-state-machine-assisted determination of food-production-machine-performance direction transmittable to one or more food production machines for performance direction thereof based upon the receiving electronic-semiconductor-transistor-voltage-level-based-state-machine-assisted reception of user-menu-selection display-choice data associated with electronic-semiconductor-transistor-voltage-level-based-state-machine-assisted collection of user-physiological information, associated with electronic-semiconductor-transistor-voltage-level-based-state-machine-assisted collection of user-conduct information, and associated with electronic-semiconductor-transistor-level-level-based-state-machine-assisted obtaining of food-based information;

electronically achieving transistor-based communication from one or more automated-food-item production locations with one or more data centers for machine-assisted updating of food-item production data at the one or more automated-food-item production locations regarding one or more aspects of machine-automated-food-item providing;

electronically performing transistor-based amalgamation of food-item production data for electronically exhibiting machine-assisted presentation of one or more updated food-item selection alternatives at the one or more automated-food-production locations based at least in part on the machine-assisted updating of the food-item-production data regarding one or more aspects of machine-automated-food-item providing;

electronically apprising the one or more data centers from the one or more automated-food-item-production locations at least in part associated with selection information received in response to the electronically exhibiting machine-assisted presentation of one or more updated food-item selection alternatives;

electronically performing transistor-based reception of first query selection data related to electronic transistor-based presentation of first query selection options regarding allocation data associated with machine-automated food allocation to one or more users;

electronically performing transistor-based reception of second query selection data related to electronic transistor-based presentation of second query selection options regarding user data associated with user parameter status of the one or more users;

electronically performing transistor-based transmission of correlation analysis data between allocation data and user data in response to transistor-based reception of the first and second query selection data;

electronically effecting state-machine-based emission of first-indication data indicative of first-requested-characteristic data descriptive of one or more human subjects elicited at least in part by electronic state-machine-based presentation of one or more characteristic-data-candidate prompts;

electronically effecting state-machine-based emission of second-indication data indicative of second-requested-food-product data descriptive of one or more food products fabricated for the one or more human subjects elicited at least in part by electronic state-machine-based presentation of one or more food-product-data-candidate prompts; and electronically effecting electronic-state-machine-based reception of electronic-state-machine-generated resultant data at least in part related to the first-requested-characteristic data descriptive of one or more human subjects and to the second-requested-food-product data descriptive of one or more food products fabricated for the one or more human subjects.

2. The computationally-implemented method of claim 1, wherein the electronically receiving user biological status information from electronically involved detection of one or more biological user conditions comprises:

electronically receiving user biological status information at least in part involving user functional status information including electronically receiving user biological status information at least in part involving user sleep status information.

3. The computationally-implemented method of claim 1, wherein the electronically receiving user biological status information from electronically involved detection of one or more biological user conditions comprises:

electronically receiving user biological status information at least in part involving user ambulatory status information including electronically receiving user biological status information at least in part involving user motor skills status information.

4. The computationally-implemented method of claim 1, wherein the electronically receiving user biological status information from electronically involved detection of one or more biological user conditions comprises:

electronically receiving from electronically involved detection of one or more biological user conditions regarding at least in part disease including electronically receiving from electronically involved detection of one or more biological user conditions regarding at least in part chronic disease.

5. The computationally-implemented method of claim 1, wherein the electronically accessing record data associated with ingestible material dispensing by one or more dispensing machines to one or more individuals comprises:

electronically accessing record data involving at least in part user related outcome including electronically accessing record data involving at least in part one or more goals of another.

6. The computationally-implemented method of claim 1, wherein the electronically accessing record data associated with ingestible material dispensing by one or more dispensing machines to one or more individuals comprises:

electronically accessing record data regarding one or more electronically controlled dispensing procedures including electronically accessing record data regarding manually oral-delivered consumable substance packaging procedures.

7. The computationally-implemented method of claim 1, wherein the electronically accessing record data associated with ingestible material dispensing by one or more dispensing machines to one or more individuals comprises:

electronically accessing biological user condition record data at least in part involving user functional status information including electronically accessing biological user condition record data at least in part involving user ambulatory status information.

8. The computationally-implemented method of claim 1, wherein the electronically performing electronic-semiconductor-transistor-based-device-assisted monitoring of user physiological aspect data of an electronic-semiconductor-transistor-based-device user involving in part orchestration of electronic-semiconductor-transistor-based voltage levels and performing electronic-semiconductor-transistor-based-device-assisted monitoring of user behavioral aspect data of the electronic-semiconductor-transistor-based-device user involving in part orchestration of electronic-semiconductor-transistor-based voltage levels comprises:

electronically monitoring of user behavioral aspect data of the electronic-semiconductor-transistor-based-device user as at least in part electronically-involved user ambulatory status monitoring including electronically monitoring of user behavioral aspect data of the electronic-semiconductor-transistor-based-device user as at least in part electronically-involved user walking performance monitoring.

9. The computationally-implemented method of claim 1, wherein the electronically performing electronic-semiconductor-transistor-based-device-assisted monitoring of user physiological aspect data of an electronic-semiconductor-transistor-based-device user involving in part orchestration of electronic-semiconductor-transistor-based voltage levels and performing electronic-semiconductor-transistor-based-device-assisted monitoring of user behavioral aspect data of the electronic-semiconductor-transistor-based-device user involving in part orchestration of electronic-semiconductor-transistor-based voltage levels comprises:

electronically monitoring of user physiological aspect data of the electronic-semiconductor-transistor-based-device user as at least in part invasive or noninvasive user physiological aspect data.

10. The computationally-implemented method of claim 1, wherein the electronically performing electronic-semiconductor-transistor-based-device-assisted monitoring of user physiological aspect data of an electronic-semiconductor-transistor-based-device user involving in part orchestration of electronic-semiconductor-transistor-based voltage levels and performing electronic-semiconductor-transistor-based-device-assisted monitoring of user behavioral aspect data of the electronic-semiconductor-transistor-based-device user involving in part orchestration of electronic-semiconductor-transistor-based voltage levels including electronically monitoring of user physiological aspect data of the electronic-semiconductor-transistor-based-device user as at least in part user physiological aspect data regarding at least in part disease comprises:

electronically monitoring of user physiological aspect data of the electronic-semiconductor-transistor-based-device user as at least in part user physiological aspect data regarding at least in part disease including electronically monitoring of user physiological aspect data of the electronic-semiconductor-transistor-based-device user as at least in part user physiological aspect data regarding at least in part life-style induced disease.

11. The computationally-implemented method of claim 1, wherein the electronically outputting electronic-semiconductor-transistor-voltage-level-based-state-machine-assisted-user-menu-selection display associated with electronic-semiconductor-transistor-voltage-level-based-state-machine-assisted collection of user-physiological information, associated with electronic-semiconductor-transistor-voltage-level-based-state-machine-assisted collection of user-conduct information, and associated with electronic-semiconductor-transistor-voltage-level-based-state-machine-assisted obtaining of food-based information comprises:

electronically outputting electronic-semiconductor-transistor-voltage-level-based-state-machine-assisted-user-menu-selection display associated with collection of user-conduct information regarding at least in part electronically-involved user performance status including electronically outputting electronic-semiconductor-transistor-voltage-level-based-state-machine-assisted-user-menu-selection display associated with collection of user-conduct information regarding at least in part electronically-involved vocationally-related user performance status.

12. The computationally-implemented method of claim 1, wherein the electronically outputting electronic-semiconductor-transistor-voltage-level-based-state-machine-assisted-user-menu-selection display associated with electronic-semiconductor-transistor-voltage-level-based-state-machine-assisted collection of user-physiological information, associated with electronic-semiconductor-transistor-voltage-level-based-state-machine-assisted collection of user-conduct information, and associated with electronic-semiconductor-transistor-voltage-level-based-state-machine-assisted obtaining of food-based information comprises:

electronically outputting electronic-semiconductor-transistor-voltage-level-based-state-machine-assisted-user-menu-selection display associated with obtaining food-based information regarding food nutrition factors from one or more food nutrition information services including electronically outputting electronic-semiconductor-transistor-voltage-level-based-state-machine-assisted-user-menu-selection display associated with obtaining food-based information for one more ingredient quantities.

13. The computationally-implemented method of claim 1, wherein the electronically receiving electronic-semiconductor-transistor-voltage-level-based-state-machine-assisted reception of user-menu-selection display-choice data associated with electronic-semiconductor-transistor-voltage-level-based-state-machine-assisted collection of user-physiological information, associated with electronic-semiconductor-transistor-voltage-level-based-state-machine-assisted collection of user-conduct information, and associated with electronic-semiconductor-transistor-level-level-based-state-machine-assisted obtaining of food-based information comprises:

electronically receiving electronic-semiconductor-transistor- voltage-level-based-state-machine-assisted reception of user-menu-selection display-choice data associated with electronic-semiconductor-transistor-voltage-level-based-state-machine-assisted collection of user-physiological information, associated with electronic-semiconductor-transistor-voltage-level-based-state-machine-assisted collection of user-conduct information, and associated with electronic-semiconductor-transistor-level-level-based-state-machine-assisted obtaining of food-based information including electronically receiving electronic-semiconductor-transistor-voltage-level-based-state-machine-assisted reception of user-menu-selection display-choice data associated with collection of physiological information and collection of user-conduct information as at least in part portable-electronically-involved monitoring.

14. The computationally-implemented method of claim 1, wherein the electronically achieving transistor-based communication from one or more automated-food-item production locations with one or more data centers for machine-assisted updating of food-item production data at the one or more automated-food-item production locations regarding one or more aspects of machine-automated-food-item providing comprises:

achieving transistor-based communication for transistor-based updating with food composition data submitted by one or more members of one or more member-based social networks including achieving transistor-based communication for transistor-based updating with food composition data involving social-network-member-submitted data on micronutrient related food ingredient availability.

15. The computationally-implemented method of claim 1, wherein the electronically achieving transistor-based communication from one or more automated-food-item production locations with one or more data centers for machine-assisted updating of food-item production data at the one or more automated-food-item production locations regarding one or more aspects of machine-automated-food-item providing comprises:

electronically achieving transistor-based communication from one or more automated-food-item production locations with one or more data centers for machine-assisted updating of food-item production data at the one or more automated-food-item production locations regarding one or more aspects of machine-automated-food-item providing including achieving transistor-based communication for transistor-based updating food composition data from one or more food material supply related electronic data centers associated with one or more recipe subscription services.

16. The computationally-implemented method of claim 1, wherein the electronically achieving transistor-based communication from one or more automated-food-item production locations with one or more data centers for machine-assisted updating of food-item production data at the one or more automated-food-item production locations regarding one or more aspects of machine-automated-food-item providing comprises:

achieving transistor-based communication for transistor-based updating food recipe related information from one or more analytical electronic data centers associated with one or more correlation studies including achieving transistor-based communication for transistor-based updating food recipe related information including correlation data regarding one or more food ingredient manufacturing procedures.

17. The computationally-implemented method of claim 1, wherein the electronically performing transistor-based reception of first query selection data related to electronic transistor-based presentation of first query selection options regarding allocation data associated with machine-automated food allocation to one or more users comprises:

electronically performing transistor-based reception of first query selection data related to electronic transistor-based presentation of first query selection options regarding allocation data associated with machine-automated food allocation to one or more users including electronically performing reception of first selection data regarding one or more user related outcome goals.

18. The computationally-implemented method of claim 1, wherein the electronically effecting state-machine-based emission of first-indication data indicative of first-requested-characteristic data descriptive of one or more human subjects elicited at least in part by electronic state-machine-based presentation of one or more characteristic-data-candidate prompts comprises:

electronically effecting state-machine-based emission of first-indication data at least in part descriptive of human subjects quantified-self information including electronically effecting state-machine-based emission of first-indication data at least in part descriptive of social network collected quantified-self metric data.

* * * * *